US012297564B2

United States Patent
Kamath et al.

(10) Patent No.: US 12,297,564 B2
(45) Date of Patent: May 13, 2025

(54) QUALITY CONTROL REAGENTS AND METHODS FOR SERUM ANTIBODY PROFILING

(71) Applicant: Serimmune Inc., Goleta, CA (US)

(72) Inventors: Kathryn Vinaya Louise Kamath, Santa Barbara, CA (US); Jack Ryan Reifert, Santa Barbara, CA (US); Patrick Sean Daugherty, Goleta, CA (US)

(73) Assignee: Serimmune Inc., Goleta, CA (US)

( * ) Notice: Subject to any disclaimer, the term of this patent is extended or adjusted under 35 U.S.C. 154(b) by 1016 days.

(21) Appl. No.: 17/267,004

(22) PCT Filed: Aug. 8, 2019

(86) PCT No.: PCT/US2019/045650
§ 371 (c)(1),
(2) Date: Feb. 8, 2021

(87) PCT Pub. No.: WO2020/033642
PCT Pub. Date: Feb. 13, 2020

(65) Prior Publication Data
US 2021/0230580 A1    Jul. 29, 2021

Related U.S. Application Data

(60) Provisional application No. 62/716,099, filed on Aug. 8, 2018.

(51) Int. Cl.
C40B 40/10    (2006.01)
C12N 15/10    (2006.01)
C40B 40/08    (2006.01)

(52) U.S. Cl.
CPC .......... C40B 40/08 (2013.01); C12N 15/1037 (2013.01); C12N 15/1072 (2013.01)

(58) Field of Classification Search
None
See application file for complete search history.

(56) References Cited

U.S. PATENT DOCUMENTS

2009/0005257 A1    1/2009  Jespers et al.
2011/0207628 A1    8/2011  Li et al.
2018/0267056 A1*   9/2018  Daugherty ........... G01N 33/569

FOREIGN PATENT DOCUMENTS

WO    WO 2017/083874 A1 *  5/2017    ............. A61K 38/02

OTHER PUBLICATIONS

PCT/US2019/045650—International Search Report and Written Opinion, Dec. 13, 2019, 13 pages.
PCT/US2019/045650—International Preliminary Report on Patentability, Feb. 9, 2021, 6 pages.
Pantazes et al., "Identification of disease-specific motifs in the antibody specificity repertoire via next-generation sequencing." Scientific reports 6, No. 1 (Aug. 2, 2016): 1-11.
(Continued)

*Primary Examiner* — Christian C Boesen
(74) *Attorney, Agent, or Firm* — Goodwin Procter LLP

(57) ABSTRACT

Disclosed herein are reagents for use in quality control assessment of antibody profiling platforms, such as biopanning and Digital Serology. Also disclosed herein are kits, method of manufacturing, and methods of using the same.

30 Claims, 6 Drawing Sheets

Figure 1:
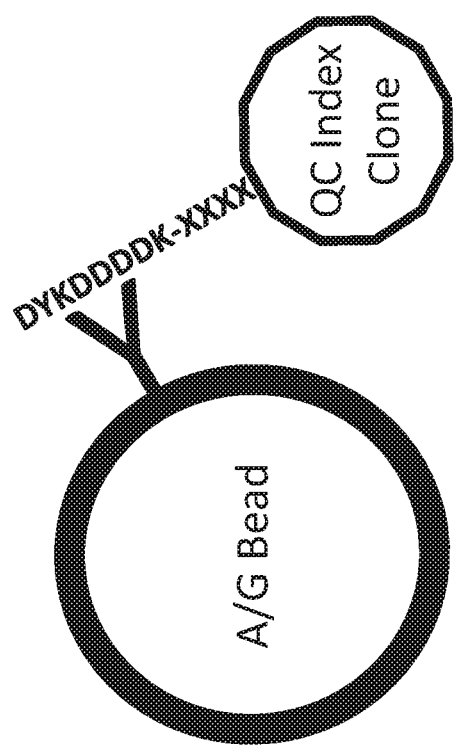

Specification includes a Sequence Listing.

(56) References Cited

OTHER PUBLICATIONS

Paull et al., "Mapping serum antibody repertoires using peptide libraries." Current opinion in chemical engineering 19 (Mar. 1, 2018): 21-26.
Weiss-Ottolenghi et al., "Profiling the IgOme: meeting the challenge." FEBS letters 588, No. 2 (2014): 318-325.

* cited by examiner

|       | QC1    | QC2    | QC3    | QC4    | QC5    | QC6    | QC7    | QC8    | QC11   | QC12   |
|-------|--------|--------|--------|--------|--------|--------|--------|--------|--------|--------|
| QC13  | 1 - 13 | 2 - 13 | 3 - 13 | 4 - 13 | 5 - 13 | 6 - 13 | 7 - 13 | 8 - 13 | 11 - 13 | 12 - 13 |
| QC14  | 1 - 14 | 2 - 14 | 3 - 14 | 4 - 14 | 5 - 14 | 6 - 14 | 7 - 14 | 8 - 14 | 11 - 14 | 12 - 14 |
| QC15  | 1 - 15 | 2 - 15 | 3 - 15 | 4 - 15 | 5 - 15 | 6 - 15 | 7 - 15 | 8 - 15 | 11 - 15 | 12 - 15 |
| QC19  | 1 - 19 | 2 - 19 | 3 - 19 | 4 - 19 | 5 - 19 | 6 - 19 | 7 - 19 | 8 - 19 | 11 - 19 | 12 - 19 |
| QC20  | 1 - 20 | 2 - 20 | 3 - 20 | 4 - 20 | 5 - 20 | 6 - 20 | 7 - 20 | 8 - 20 | 11 - 20 | 12 - 20 |
| QC21  | 1 - 21 | 2 - 21 | 3 - 21 | 4 - 21 | 5 - 21 | 6 - 21 | 7 - 21 | 8 - 21 | 11 - 21 | 12 - 21 |
| QC22  | 1 - 22 | 2 - 22 | 3 - 22 | 4 - 22 | 5 - 22 | 6 - 22 | 7 - 22 | 8 - 22 | 11 - 22 | 12 - 22 |
| QC23  | 1 - 23 | 2 - 23 | 3 - 23 | 4 - 23 | 5 - 23 | 6 - 23 | 7 - 23 | 8 - 23 | 11 - 23 | 12 - 23 |

FIG. 5

SEQUENCE LISTING

```
<160> NUMBER OF SEQ ID NOS: 85

<210> SEQ ID NO 1
<211> LENGTH: 53
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base
<222> LOCATION: (34)..(38)
<223> OTHER INFORMATION: a, c, t, g, unknown or other

<400> SEQUENCE: 1
```
tcgtcggcag cgtcagatgt gtataagaga cagnnnnncc agtctggcca ggg    53

<210> SEQ ID NO 2
<211> LENGTH: 54
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 2
ccagtactac ggcatcactg ctgtctctta tacacatctc cgagcccacg agac    54

<210> SEQ ID NO 3
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 3

Asp Tyr Lys Asp Asp Asp Asp Lys
1               5

<210> SEQ ID NO 4
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 4

Glu Gln Lys Leu Ile Ser Glu Glu Asp Leu
1               5                   10

<210> SEQ ID NO 5
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 5

Tyr Pro Tyr Asp Val Pro Asp Tyr Ala
1               5

<210> SEQ ID NO 6
<211> LENGTH: 6
<212> TYPE: PRT
<213> ORGANISM: Artificial Sequence
<220> FEATURE:
<223> OTHER INFORMATION: Description of Artificial Sequence: Synthetic
      6xHis tag

<400> SEQUENCE: 6

His His His His His His
1               5

<210> SEQ ID NO 7
<211> LENGTH: 21
<212> TYPE: PRT
<213> ORGANISM: Artificial Sequence
<220> FEATURE:
<223> OTHER INFORMATION: Description of Artificial Sequence: Synthetic peptide

<400> SEQUENCE: 7

Asp Tyr Lys Asp His Asp Gly Asp Tyr Lys Asp His Asp Ile Asp Tyr
1               5                   10                  15

Lys Asp Asp Asp Lys
            20

<210> SEQ ID NO 8
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 8

Gly Lys Pro Ile Pro Asn Pro Leu Leu Gly Leu Asp Ser Thr
1               5                   10

<210> SEQ ID NO 9
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 9

Tyr Thr Asp Ile Glu Met Asn Arg Leu Gly Lys
1               5                   10

<210> SEQ ID NO 10
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 10

Asp Tyr Lys Asp Asp Asp Asp Lys Thr Ser Asn Gln
1               5                   10

<210> SEQ ID NO 11
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 11

Asp Tyr Lys Asp Asp Asp Asp Lys Thr Ser Gln Asn
1               5                   10

<210> SEQ ID NO 12
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 12

Asp Tyr Lys Asp Asp Asp Asp Lys Thr Gln Asn Ser
1               5                   10

<210> SEQ ID NO 13
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 13

Asp Tyr Lys Asp Asp Asp Asp Lys Thr Gln Ser Asn
1               5                   10

<210> SEQ ID NO 14
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 14

Asp Tyr Lys Asp Asp Asp Asp Lys Thr Asn Gln Ser
1               5                   10

<210> SEQ ID NO 15
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 15

Asp Tyr Lys Asp Asp Asp Asp Lys Thr Asn Ser Gln
1               5                   10

<210> SEQ ID NO 16
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 16

Asp Tyr Lys Asp Asp Asp Asp Lys Asn Ser Thr Gln
1               5                   10

<210> SEQ ID NO 17
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 17

Asp Tyr Lys Asp Asp Asp Asp Lys Asn Ser Gln Thr
1               5                   10

<210> SEQ ID NO 18
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

```
<400> SEQUENCE: 18

Asp Tyr Lys Asp Asp Asp Lys Asn Thr Gln Ser
1               5                   10

<210> SEQ ID NO 19
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 19

Asp Tyr Lys Asp Asp Asp Asp Lys Asn Thr Ser Gln
1               5                   10

<210> SEQ ID NO 20
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 20

Asp Tyr Lys Asp Asp Asp Asp Lys Asn Gln Thr Ser
1               5                   10

<210> SEQ ID NO 21
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 21

Asp Tyr Lys Asp Asp Asp Asp Lys Asn Gln Ser Thr
1               5                   10

<210> SEQ ID NO 22
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 22

Asp Tyr Lys Asp Asp Asp Asp Lys Gln Thr Asn Ser
1               5                   10

<210> SEQ ID NO 23
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 23

Asp Tyr Lys Asp Asp Asp Asp Lys Gln Thr Ser Asn
1               5                   10

<210> SEQ ID NO 24
<211> LENGTH: 12
```

```
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 24

Asp Tyr Lys Asp Asp Asp Asp Lys Gln Ser Asn Thr
1               5                   10

<210> SEQ ID NO 25
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 25

Asp Tyr Lys Asp Asp Asp Asp Lys Gln Ser Thr Asn
1               5                   10

<210> SEQ ID NO 26
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 26

Asp Tyr Lys Asp Asp Asp Asp Lys Gln Asn Thr Ser
1               5                   10

<210> SEQ ID NO 27
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 27

Asp Tyr Lys Asp Asp Asp Asp Lys Gln Asn Ser Thr
1               5                   10

<210> SEQ ID NO 28
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 28

Asp Tyr Lys Asp Asp Asp Asp Lys Ser Gln Asn Thr
1               5                   10

<210> SEQ ID NO 29
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 29

Asp Tyr Lys Asp Asp Asp Asp Lys Ser Gln Thr Asn
```

```
1               5                   10
```

<210> SEQ ID NO 30
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 30

```
Asp Tyr Lys Asp Asp Asp Asp Lys Ser Asn Thr Gln
1               5                   10
```

<210> SEQ ID NO 31
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 31

```
Asp Tyr Lys Asp Asp Asp Asp Lys Ser Asn Gln Thr
1               5                   10
```

<210> SEQ ID NO 32
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 32

```
Asp Tyr Lys Asp Asp Asp Asp Lys Ser Thr Gln Asn
1               5                   10
```

<210> SEQ ID NO 33
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 33

```
Asp Tyr Lys Asp Asp Asp Asp Lys Ser Thr Asn Gln
1               5                   10
```

<210> SEQ ID NO 34
<211> LENGTH: 36
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 34

```
gactataagg acgatgatga caaaacaagt aatcag                           36
```

<210> SEQ ID NO 35
<211> LENGTH: 36
<212> TYPE: DNA
<213> ORGANISM: Artificial Sequence
<220> FEATURE:
<223> OTHER INFORMATION: Description of Artificial Sequence: Synthetic
      oligonucleotide

```
<400> SEQUENCE: 35
gattacaagg atgatgacga taaaacatcg caaaat                                36

<210> SEQ ID NO 36
<211> LENGTH: 36
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 36
gattacaaag acgatgacga caaaacccag aactcg                                36

<210> SEQ ID NO 37
<211> LENGTH: 36
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 37
gactataaag atgacgatga caagacgcaa agcaat                                36

<210> SEQ ID NO 38
<211> LENGTH: 36
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 38
gactataaag acgacgatga taaaactaat caatca                                36

<210> SEQ ID NO 39
<211> LENGTH: 36
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 39
gactataaag atgacgatga taagactaac tcgcaa                                36

<210> SEQ ID NO 40
<211> LENGTH: 36
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 40
gattacaagg atgatgatga caaaaatagc acgcaa                                36

<210> SEQ ID NO 41
<211> LENGTH: 36
<212> TYPE: DNA
<213> ORGANISM: Artificial Sequence
<220> FEATURE:
<223> OTHER INFORMATION: Description of Artificial Sequence: Synthetic
      oligonucleotide
```

<400> SEQUENCE: 41
gactataagg atgacgacga caaaaactcc caaaca          36

<210> SEQ ID NO 42
<211> LENGTH: 36
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 42
gattacaagg acgacgacga taaaaacaca caaagt          36

<210> SEQ ID NO 43
<211> LENGTH: 36
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 43
gactataaag acgacgatga taagaatacc tctcaa          36

<210> SEQ ID NO 44
<211> LENGTH: 36
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 44
gactacaaag acgatgacga caaaaatcag acgagt          36

<210> SEQ ID NO 45
<211> LENGTH: 36
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 45
gactataaag atgacgacga taagaatcag tcaact          36

<210> SEQ ID NO 46
<211> LENGTH: 36
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 46
gactataagg atgatgacga taaacagacg aacagt          36

<210> SEQ ID NO 47
<211> LENGTH: 36
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 47

```
gattacaaag atgacgatga caaacaaaca agcaat                                      36

<210> SEQ ID NO 48
<211> LENGTH: 36
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 48
gattacaagg acgacgatga taagcagtcc aatacc                                      36

<210> SEQ ID NO 49
<211> LENGTH: 36
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 49
gactataagg atgatgatga caaacaatcc acgaat                                      36

<210> SEQ ID NO 50
<211> LENGTH: 36
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 50
gactataaag atgacgatga taagcaaaac acctcc                                      36

<210> SEQ ID NO 51
<211> LENGTH: 36
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 51
gactacaaag acgacgacga taaacagaac agcaca                                      36

<210> SEQ ID NO 52
<211> LENGTH: 36
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 52
gactataaag atgatgatga caaatcacag aataca                                      36

<210> SEQ ID NO 53
<211> LENGTH: 36
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 53
```
gattacaagg atgacgatga caagtcacag actaat                                    36

<210> SEQ ID NO 54
<211> LENGTH: 36
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 54
gactacaaag acgacgacga taagtccaat actcaa                                    36

<210> SEQ ID NO 55
<211> LENGTH: 36
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 55
gattacaagg atgatgatga caaaagcaat caaacg                                    36

<210> SEQ ID NO 56
<211> LENGTH: 36
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 56
gactataagg acgacgacga caaatcaact caaaac                                    36

<210> SEQ ID NO 57
<211> LENGTH: 36
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 57
gactacaagg atgacgatga taagtcaact aatcaa                                    36

<210> SEQ ID NO 58
<211> LENGTH: 91
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 58
acttccgtag ctggccagtc tggccagggt ggagactata aggacgatga tgacaaaaca          60
agtaatcagg gagggcagtc tgggcagtct g                                         91

<210> SEQ ID NO 59
<211> LENGTH: 91
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 59

```
acttccgtag ctggccagtc tggccagggt ggagattaca aggatgatga cgataaaaca    60
tcgcaaaatg gagggcagtc tgggcagtct g                                    91
```

<210> SEQ ID NO 60
<211> LENGTH: 91
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 60

```
acttccgtag ctggccagtc tggccagggt ggagattaca aagacgatga cgacaaaacc    60
cagaactcgg gagggcagtc tgggcagtct g                                    91
```

<210> SEQ ID NO 61
<211> LENGTH: 91
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 61

```
acttccgtag ctggccagtc tggccagggt ggagactata aagatgacga tgacaagacg    60
caaagcaatg gagggcagtc tgggcagtct g                                    91
```

<210> SEQ ID NO 62
<211> LENGTH: 91
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 62

```
acttccgtag ctggccagtc tggccagggt ggagactata aagacgacga tgataaaact    60
aatcaatcag gagggcagtc tgggcagtct g                                    91
```

<210> SEQ ID NO 63
<211> LENGTH: 91
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 63

```
acttccgtag ctggccagtc tggccagggt ggagactata aagatgacga tgataagact    60
aactcgcaag gagggcagtc tgggcagtct g                                    91
```

<210> SEQ ID NO 64
<211> LENGTH: 91
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 64

```
acttccgtag ctggccagtc tggccagggt ggagattaca aggatgatga tgacaaaaat    60
agcacgcaag gagggcagtc tgggcagtct g                                    91
```

<210> SEQ ID NO 65
<211> LENGTH: 91
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 65
acttccgtag ctggccagtc tggccagggt ggagactata aggatgacga cgacaaaaac    60
tcccaaacag gagggcagtc tgggcagtct g                                   91

<210> SEQ ID NO 66
<211> LENGTH: 91
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 66
acttccgtag ctggccagtc tggccagggt ggagattaca aggacgacga cgataaaaac    60
acacaaagtg gagggcagtc tgggcagtct g                                   91

<210> SEQ ID NO 67
<211> LENGTH: 91
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 67
acttccgtag ctggccagtc tggccagggt ggagactata aagacgacga tgataagaat    60
acctctcaag gagggcagtc tgggcagtct g                                   91

<210> SEQ ID NO 68
<211> LENGTH: 91
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 68
acttccgtag ctggccagtc tggccagggt ggagactaca aagacgatga cgacaaaaat    60
cagacgagtg gagggcagtc tgggcagtct g                                   91

<210> SEQ ID NO 69
<211> LENGTH: 91
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 69
acttccgtag ctggccagtc tggccagggt ggagactata aagatgacga cgataagaat    60
cagtcaactg gagggcagtc tgggcagtct g                                   91

<210> SEQ ID NO 70
<211> LENGTH: 91

<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 70
acttccgtag ctggccagtc tggccagggt ggagactata aggatgatga cgataaacag    60
acgaacagtg gagggcagtc tgggcagtct g                                   91

<210> SEQ ID NO 71
<211> LENGTH: 91
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 71
acttccgtag ctggccagtc tggccagggt ggagattaca aagatgacga tgacaaacaa    60
acaagcaatg gagggcagtc tgggcagtct g                                   91

<210> SEQ ID NO 72
<211> LENGTH: 91
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 72
acttccgtag ctggccagtc tggccagggt ggagattaca aggacgacga tgataagcag    60
tccaataccg gagggcagtc tgggcagtct g                                   91

<210> SEQ ID NO 73
<211> LENGTH: 91
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 73
acttccgtag ctggccagtc tggccagggt ggagactata aggatgatga tgacaaacaa    60
tccacgaatg gagggcagtc tgggcagtct g                                   91

<210> SEQ ID NO 74
<211> LENGTH: 91
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 74
acttccgtag ctggccagtc tggccagggt ggagactata aagatgacga tgataagcaa    60
aacacctccg gagggcagtc tgggcagtct g                                   91

<210> SEQ ID NO 75
<211> LENGTH: 91
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 75
acttccgtag ctggccagtc tggccagggt ggagactaca aagacgacga cgataaacag    60
aacagcacag gagggcagtc tgggcagtct g                                    91

<210> SEQ ID NO 76
<211> LENGTH: 91
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 76
acttccgtag ctggccagtc tggccagggt ggagactata aagatgatga tgacaaatca    60
cagaatacag gagggcagtc tgggcagtct g                                    91

<210> SEQ ID NO 77
<211> LENGTH: 91
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 77
acttccgtag ctggccagtc tggccagggt ggagattaca aggatgacga tgacaagtca    60
cagactaatg gagggcagtc tgggcagtct g                                    91

<210> SEQ ID NO 78
<211> LENGTH: 91
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 78
acttccgtag ctggccagtc tggccagggt ggagactaca aagacgacga cgataagtcc    60
aatactcaag gagggcagtc tgggcagtct g                                    91

<210> SEQ ID NO 79
<211> LENGTH: 91
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 79
acttccgtag ctggccagtc tggccagggt ggagattaca aggatgatga tgacaaaagc    60
aatcaaacgg gagggcagtc tgggcagtct g                                    91

<210> SEQ ID NO 80
<211> LENGTH: 91
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 80
acttccgtag ctggccagtc tggccagggt ggagactata aggacgacga cgacaaatca    60
actcaaaacg gagggcagtc tgggcagtct g    91

<210> SEQ ID NO 81
<211> LENGTH: 91
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 81
acttccgtag ctggccagtc tggccagggt ggagactaca aggatgacga tgataagtca    60
actaatcaag gagggcagtc tgggcagtct g    91

<210> SEQ ID NO 82
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(4)
<223> OTHER INFORMATION: Any amino acid
<220> FEATURE:
<221> NAME/KEY: MOD_RES
<222> LOCATION: (7)..(7)
<223> OTHER INFORMATION: Any amino acid
<220> FEATURE:
<221> NAME/KEY: MOD_RES
<222> LOCATION: (8)..(8)
<223> OTHER INFORMATION: Glu or Asp

<400> SEQUENCE: 82

Gln Pro Xaa Xaa Pro Phe Xaa Xaa
1               5

<210> SEQ ID NO 83
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 83

Thr Ser Asn Gln
1

<210> SEQ ID NO 84
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 84

Asp Asp Asp Asp Lys
1               5

<210> SEQ ID NO 85
<211> LENGTH: 12
<212> TYPE: PRT
<213> ORGANISM: Artificial Sequence
<220> FEATURE:

```
<223> OTHER INFORMATION: Description of Artificial Sequence: Synthetic
      peptide
<220> FEATURE:
<221> NAME/KEY: MOD_RES
<222> LOCATION: (9)..(12)
<223> OTHER INFORMATION: Any amino acid

<400> SEQUENCE: 85

Asp Tyr Lys Asp Asp Asp Asp Lys Xaa Xaa Xaa Xaa
1               5                   10
```

QUALITY CONTROL REAGENTS AND METHODS FOR SERUM ANTIBODY PROFILING

1. CROSS REFERENCE TO RELATED APPLICATIONS

This application is the National Stage of International Application No. PCT/US19/45650, filed Aug. 8, 2019, which claims the benefit of U.S. Provisional Application No. 62/716,099 filed Aug. 8, 2018, each of which is hereby incorporated in its entirety by reference for all purposes.

2. SEQUENCE LISTING

The instant application contains a Sequence Listing which has been submitted via EFS-Web and is hereby incorporated by reference in its entirety. Said ASCII copy, created on Oct. 4, 2019, is named SUI-002WO_Sequence_Listing.txt, and is 22,817 bytes in size.

3. BACKGROUND

Serology is the practice of identifying components of serum samples. In particular, several technologies exist in the field for identifying antibodies present in serum. For example, biopanning using peptide displays is a technique used to enrich for antibodies specific to particular protein targets. Biopanning assays have also been applied to epitope identification.

Many biopanning assays described in the field use phage display libraries and take advantage of improvements in next generation sequencing (NGS) technologies. NGS technologies allow for the possibility of screening a very large number of candidates simultaneously and thus are conducive to high-throughput large scale screens. Quality controls have been developed that provide a read-out of assay quality of the NGS sequencing step based on sequencing data. For example, a spike-in DNA control, such as DNA of bacteriophage φ174, is often used as a reference to ensure the quality of only an NGS sequencing run (Endrullat, et al.). While a DNA standard spiked into a biopanning assay samples prior to PCR can assess the NGS data, the standard does not serve as an indicator of others steps of the biopanning assay, such as efficient affinity selection, plasmid preparation or PCR amplification.

Absent from the field are standardized quality control procedures or methods that assess all steps of biopanning using NGS technologies.

4. SUMMARY

The invention described herein provides compositions and methods for assessing the validity of multiple steps of biopanning using NGS technologies.

Accordingly, disclosed herein is a peptide expression library composition comprising: a) a library of nucleic acid sequences encoding a library of peptides; b) one or more control vectors comprising: 1) a nucleic acid sequence encoding a control binding target of a control binding molecule, wherein the control binding target is identical for each of the control vectors, and 2) a unique nucleic acid sequence, wherein the unique nucleic acid sequence is specific for each of the control vectors.

Also disclosed herein is peptide library composition comprising: a) a library of nucleic acid sequences encoding a library of random peptides; b) two control vectors, each comprising: 1) a nucleic acid sequence encoding an epitope sequence that is a known binding target of a control binding molecule, wherein the control binding molecule comprises an antibody or fragment thereof, wherein the epitope sequence is identical for each of the control vectors, and 2) a unique nucleic acid sequence, wherein the unique nucleic acid sequence is specific for each of the control vectors, and c) two or more array surfaces, wherein the library of random peptides and the epitope sequence are capable of being expressed, and wherein each of the array surfaces is configured to display multiple copies of: 1) one of the random peptides, or 2) the epitope sequence encoded by one of the control vectors.

In some aspects, the composition further comprises two or more array surfaces, wherein each of the array surfaces is configured to display one or more copies of either: 1) one of the peptides of the library of peptides, or 2) the control binding target encoded by one of the control vectors.

In some aspects, the library of peptides is a random peptide library. In some aspects, the library of peptides is a non-random peptide library. In some aspects, the non-random library is biased to represent one or more diseases or conditions.

In some aspects, each of the peptides in the library of peptides is at least 5, 6, 7, 8, 9, 10, 11, 12, 13, 14, 15, 16, 17, 18, 19, or 20 amino acids in length. In some aspects, each of the peptides in the library of peptides is an identical defined length. In some aspects, the identical defined length is 5, 6, 7, 8, 9, 10, 11, 12, 13, 14, 15, 16, 17, 18, 19, or 20 amino acids in length. In some aspects, the identical defined length is 12 amino acids in length.

In some aspects, the library of peptides is selected from the group consisting of: a bacterial expression library, a yeast expression library, a bacteriophage expression library, and a mammalian expression library.

In some aspects, the control binding target comprises a defined peptide sequence. In some aspects, the defined peptide sequence comprises an epitope sequence. In some aspects, the epitope sequence is not derived from an antigen generally encountered in a human population. In some aspects, the antigen generally encountered in the human population is associated with a human pathogen. In some aspects, the antigen generally encountered in the human population is present in the human population at a frequency greater than 1 in 1000, greater than 1 in 10^4, greater than 1 in 10^5, or greater than 1 in 10^6. In some aspects, the epitope sequence is selected from the group consisting of: FLAG (DYKDDDDK, SEQ ID NO:3), Myc (EQKLISEEDL, SEQ ID NO:4), HA (YPYDVPDYA, SEQ ID NO:5), His (HHHHHH, SEQ ID NO:6), 3X-FLAG (DYKDHDGDYKDHDIDYKDDDK, SEQ ID NO:7), V5 (GKPIPNPLLGLDST, SEQ ID NO:8), and VSV-G (YTDIEMNRLGK, SEQ ID NO:9). In some aspects, the control binding target comprises an aptamer, a peptoid, or an affibody target sequence.

In some aspects, the control binding molecule comprises an antibody or fragment thereof. In some aspects, the control binding molecule is an antibody or fragment thereof. In some aspects, the control binding molecule is an aptamer, a peptoid, or an affibody.

In some aspects, the control binding molecule is bound to or capable of being bound to a capture entity. In some aspects, the capture entity comprises a solid support selected from the group consisting of: an agarose bead, a sepharose bead, a magnetic bead, and a resin. In some aspects, the capture entity comprises a binding moiety that binds to the control binding molecule. In some aspects, the binding moiety is selected from the group consisting of: Protein A, Protein G, Protein A/G, and an anti-immunoglobulin antibody. In some aspects, the binding moiety comprises streptavidin and the control binding molecule further comprises biotin. In some aspects, the capture entity further comprises a fluorophore.

In some aspects, each of the unique nucleic acid sequences is at least 4, 5, 6, 7, 8, 9, 10, 11, 12, 13, 14, 15, 16, 17, 18, 19, 20, 21, 22, 23, 24, 25, 26, 27, 28, 29, or 30 nucleotides in length. In some aspects, each of the unique nucleic acid sequences is an identical defined length. In some aspects, the identical defined length is 4, 5, 6, 7, 8, 9, 10, 11, 12, 13, 14, 15, 16, 17, 18, 19, 20, 21, 22, 23, 24, 25, 26, 27, 28, 29, or 30 nucleotides in length. In some aspects, the identical defined length is at least 12 nucleotides in length. In some aspects, the identical defined length is 12 nucleotides in length.

In some aspects, each of the unique nucleic acid sequences differ by at least 2, at least 3, at least 4, at least 5, at least 6, at least 7, at least 8, at least 9, at least 10-15, at least 15-20, or at least 20-30 nucleotides. In some aspects, each of the unique nucleic acid sequences differ by at least 2 nucleotides.

In some aspects, the unique nucleic acid sequence encodes a unique peptide sequence expressed a part of the defined peptide sequence. In some aspects, the control binding target comprises a defined peptide sequence, and the unique peptide sequence is capable of being expressed as part of a polypeptide comprising the defined peptide sequence. In some aspects, wherein each of the unique peptide sequences is at least 5, 6, 7, 8, 9, 10, 11, 12, 13, 14, 15, 16, 17, 18, 19, or 20 amino acids in length. In some aspects, each of the unique peptide sequences is an identical defined length. In some aspects, the identical defined length is 3, 4, 5, 6, 7, 8, 9, 10, 11, 12, 13, 14, 15, 16, 17, 18, 19, or 20 amino acids in length. In some aspects, the identical defined length is 4 amino acids in length. In some aspects, at least 2 of the unique peptide sequences comprises an identical amino acid composition. In some aspects, each of the unique peptide sequences comprises an identical amino acid composition. In some aspects, an order of amino acids in the identical amino acid composition is unique for each of the unique peptide sequences comprising the identical amino acid composition. In some aspects, the number of unique amino acids in the unique peptide sequences with the identical amino acid composition is equivalent to the defined length of the unique peptide sequence. In some aspects, each of the unique peptide sequences comprises a unique amino acid composition.

In some aspects, the defined peptide sequence and the unique peptide sequence are immediately adjacent to each other. In some aspects, the defined peptide sequence and the unique peptide sequence are separated by an additional peptide sequence. In some aspects, the defined peptide sequence is N-terminal or C-terminal of the unique peptide sequence.

In some aspects, the composition comprises two or more control vectors. In some aspects, the composition comprises two control vectors.

In some aspects, a total number of nucleic acid sequences in the library of nucleic acid sequences and a total number of each of the one or more control vectors is at a defined ratio. In some aspects, the defined ratio of the total number of nucleic acid sequences in the library of nucleic acid sequences to the total number of each of the one or more control vectors is between $1\times10^4$ and $1\times10^8$. In some aspects, the defined ratio of the total number of nucleic acid sequences in the library of nucleic acid sequences to the total number of each of the one or more control vectors is about $1\times10^4$, about $1\times10^5$, about $1\times10^6$, about $1\times10^7$, or about $1\times10^8$. In some aspects, the defined ratio of the total number of nucleic acid sequences in the library of nucleic acid sequences to the total number of each of the one or more control vectors is at least $1\times10^4$, at least $5\times10^4$, at least $7.5\times10^4$, or at least $1\times10^5$. In some aspects, wherein the defined ratio of the total number of nucleic acid sequences in the library of nucleic acid sequences to the total number of each of the one or more control vectors is at least $1\times10^5$, at least $1\times10^6$, at least $1\times10^7$, or at least $1\times10^8$. In some aspects, the defined ratio of the total number of nucleic acid sequences in the library of nucleic acid sequences to the total number of each of the one or more control vectors is about $7.7\times10^4$.

In some aspects, the total number of each of the one or more control vectors is about $1\times10^4$, about $1\times10^5$, about $1\times10^6$, about $1\times10^7$, or about $1\times10^8$. In some aspects, the total number of each of the one or more control vectors is at least $1\times10^4$, at least $1\times10^5$, at least $1\times10^6$, at least $1\times10^7$, or at least $1\times10^8$. In some aspects, the total number of each of the one or more control vectors is at least $1\times10^6$.

In some aspects, the composition further comprises one or more second control vectors, each of the second control vectors comprising: 1) a nucleic acid sequence encoding a second control binding target of a second control binding molecule, wherein the second control binding target is identical for each of the second control vectors, and 2) a unique nucleic acid sequence, wherein the unique nucleic acid sequence is specific for each of the second control vectors.

In some aspects, the two or more array surfaces comprises a biological entity surface. In some aspects, the biological entity is selected from the group consisting of: a mammalian cell, a yeast, a bacteria, a virus, and a bacteriophage.

In some aspects, each nucleic acid sequence encoding a peptide sequence comprises a nucleic acid sequence encoding a cell surface display peptide sequence configured to be expressed as part of the peptide and capable of directing the peptides for display on the biological entity surface.

In some aspects, displaying comprises presentation of each peptide for direct binding by the control binding molecule.

In some aspects, each of the nucleic acid sequences encoding the library of peptides and each of the control binding targets is operably linked to at least one promoter. In some aspects, the at least one promoter is a constitutive promoter. In some aspects, the at least one promoter is an inducible promoter.

In some aspects, the nucleic acid sequences encoding the library of peptides, the nucleic acid sequences encoding the control binding targets, and the unique nucleic acid sequences each further comprise polymerase chain reaction (PCR) primer target sequences configured for amplification of the nucleic acid sequences encoding the library of peptides, the nucleic acid sequences encoding the control binding targets, and the unique nucleic acid sequences.

Also disclosed herein is a composition comprising two or more of the peptide expression library compositions of any one of the peptide library compositions described herein. In some aspects, each of the two or more of the peptide expression library compositions is in a separate container. In some aspects, the container is selected from the group consisting of: a well in a multi-well plate, a microcentrifuge tube, a test tube, a tube, and a PCR tube. In some aspects, the two or more of the peptide expression library compositions is 2, 3, 4, 5, 6, 7, 8, 9, 10-15, 16-24, 24-48, 48-96, or 96-384 peptide expression library compositions. In some aspects, the two or more of the peptide expression library compositions is at least 10, at least 20, at least 50, at least 100, at least 200, at least 300, at least 500, at least 1000, or at least 2000 expression library compositions. In some aspects, the unique nucleic acid sequence is unique for each of the two or more of the peptide expression library compositions. In some aspects, each of the two or more of the peptide expression library compositions comprise two or more control vectors, wherein a combination of the unique nucleic acid sequences associated with the two or more control vectors are configured to uniquely identify each of the two or more of the peptide expression library compositions.

Also disclosed herein is a kit comprising the composition of any of the compositions described herein and instructions for use.

Also disclosed herein is a method of manufacturing any of the compositions described herein or kits described herein.

Also disclosed herein is a method of assay quality control comprising the steps of: a) providing a sample known or suspected to have specimen binding molecules, b) providing the peptide expression library composition of any of the compositions described herein, wherein the library of peptides is expressed, the control binding target is expressed, and wherein each of the array surfaces displays one or more copies of: 1) one of the peptides of the library of peptides, or 2) the control binding target, and wherein the unique nucleic acid sequences of the one or more control vectors is specific for the sample; c) providing the control binding molecule, and d) contacting the sample with the peptide expression library composition and the control binding molecule under conditions that promote binding of the control binding molecule to the control binding target.

In some aspects, the method further comprises the steps (e)-(g) of: e) isolating the specimen binding molecules and the control binding molecules bound to peptides bound to peptides, f) determining: 1) the unique nucleic acid sequences specific for each of the control vectors encoding the control binding targets bound by the isolated control binding molecules, and 2) unique nucleic acid sequences associated with one or more control vectors that are not specific for the sample, optionally wherein the unique nucleic acid sequences not specific for the sample express the control binding target bound by the isolated control binding molecules, and g) assessing or having assessed from step (f) whether the determined nucleic acid sequences meet a quality control standard. In some aspects, the determining step (f) comprises calculating a percentage of the unique nucleic acid sequences specific for the sample present relative to a total number of unique nucleic acid sequences, wherein the total number comprises the number of the unique nucleic acid sequences specific for the sample and the number of the unique nucleic acid sequences not specific for the sample. In some aspects, the quality control standard comprises a contamination threshold, and wherein a percentage below the contamination threshold indicates contamination of the sample in any one of steps a-f. In some aspects, the contamination threshold is between 90-100%, between 92-100%, between 95-100%, between 96-100%, or between 98-100%. In some aspects, the quality control standard is at least 90%, at least 92%, at least 95%, at least 96%, at least 97%, at least 98%, or at least 99%. In some aspects, the contamination threshold is at least 98%. In some aspects, the contamination threshold is 98%.

In some aspects, the method further comprises the steps (e)-(g) of: e) isolating the specimen binding molecules and the control binding molecules bound to peptides, f) determining: 1) the unique nucleic acid sequences specific for each of the control vectors encoding the control binding target bound by the isolated control binding molecules, and 2) the nucleic acid sequences encoding a peptide bound by the isolated specimen binding molecules, and g) assessing or having assessed from step (f) whether the determined nucleic acid sequences meet a quality control standard. In some aspects, the determining comprises calculating a percentage of the unique nucleic acid sequences specific for a sample relative to a total number of nucleic acid sequences, the total number comprising the number of the unique nucleic acid sequences specific and not specific for the sample and the number of nucleic acid sequences encoding the peptides in the library of peptides. In some aspects, the quality control standard comprises an error threshold, and wherein a percentage above or below the error threshold indicates an error occurred in any one of steps a-f. In some aspects, the error threshold is between 0.01%-2.0%, between 0.05%-2.0%, or between 0.01%-1.0%. In some aspects, the error threshold is between 0.05%-1.0%.

In some aspects, the sample is selected from the group consisting of: serum, blood, saliva, urine, tissue, tissue homogenates, stool, spinal fluid, and lysate derived from animal sources. In some aspects, the sample is human serum. In some aspects, the human serum is from a subject suspected of having a disease. In some aspects, the disease is selected from the group consisting of: a bacterial infection, a viral infection, a parasitic infection, an autoimmune disorder, cancer, and an allergy. In some aspects, the binding molecules in the sample are antibodies. In some aspects, the antibodies comprise one or more antibodies that recognize antigens or epitopes correlating with a disease. In some aspects, the disease is selected from the group consisting of: a bacterial infection, a viral infection, a parasitic infection, an autoimmune disorder, cancer, and an allergy.

In some aspects, the contacting comprises mixing the sample, the peptide expression library composition, and the control binding molecule in a container selected from the group consisting of: a well in a multi-well plate, a microcentrifuge tube, a test tube, a tube, and a PCR tube.

In some aspects, the isolating step (e) is selected from the group consisting of: magnetic isolation, bead centrifugation, resin centrifugation, and flow cytometry. In some aspects, the isolating step (e) comprises contacting the sample with a capture entity. In some aspects, the capture entity is selected from the group consisting of: an agarose bead, a sepharose bead, a magnetic bead, and a resin. In some aspects, the capture entity comprises a binding moiety. In some aspects, the binding moiety is selected from the group consisting of: Protein A, Protein G, Protein A/G, an anti-immunoglobulin antibody. In some aspects, the binding moiety comprises streptavidin and the control binding molecule, the specimen binding molecules, or the control binding molecule and the specimen binding molecules further comprises biotin.

In some aspects, the array surface is a biological entity surface.

In some aspects, the determining step further comprises the steps of: 1) purifying or having purified polynucleotides from the biological entity, wherein the polynucleotides comprise the unique nucleic acid sequences and the nucleic acid sequences encoding a peptide bound by the isolated specimen binding molecules; 2) amplifying or having amplified the unique nucleic acid sequences and optionally the nucleic acid sequences encoding a peptide bound by the isolated specimen binding molecules; and 2) sequencing or having sequenced the amplified polynucleotides. In some aspects, the amplifying step further comprises adding a sample identifying nucleic acid sequence to a terminus of the amplified polynucleotides, wherein the sample identifying nucleic acid sequence is unique to the sample. In some aspects, the method further comprises the step of determining the identity of the sample identifying nucleic acid sequences. In some aspects, the method further comprises the step assessing or having assessed whether the identity of the sample identifying nucleic acid sequences meets a quality control standard. In some aspects, the quality control standard comprises a post-amplification contamination threshold, wherein the post-amplification contamination threshold comprises the identity of the sample identifying nucleic acid sequence, and wherein presence of an unexpected sample identifying nucleic acid sequence indicates contamination of the sample.

5. BRIEF DESCRIPTION OF THE SEVERAL VIEWS OF THE DRAWINGS

These and other features, aspects, and advantages of the present invention will become better understood with regard to the following description, and accompanying drawings, where:

FIG. 1 illustrates the general configuration of the QC index bacterial clones using the Flag epitope/antibody system used in a Quality Control (QC) index system. The Quality Control (QC) index system generally comprises:
1) Each tube or well of the 96 well assay plate contains:
   Peptide display library
   2 peptide expressing QC index bacterial clones which represent a well-specific QC index pair=common Flag tag (DYKDDDDK (SEQ ID NO:3))-4 unique amino acids (XXXX) ("DYKDDDDKXXXX" is disclosed as SEQ ID NO:85)
2) All serum is diluted in buffer containing a Flag antibody
   Spiked serum is incubated in wells and antibodies bind peptides on bacteria that resemble their epitopes
   Flag antibody binds to bacterial QC clones that contain the Flag epitope
3) A/G beads are added
   Flag antibody—peptide-clones are captured on beads along with serum antibodies.

Figure 2:
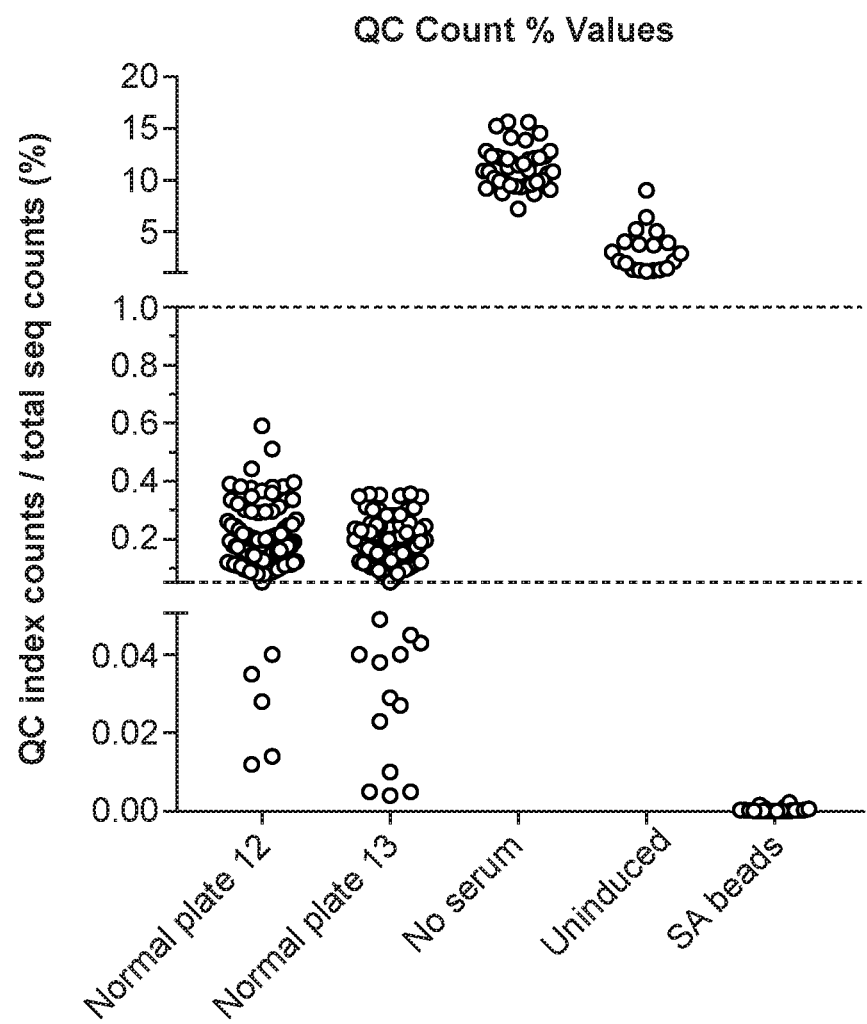

FIG. 2 demonstrates results from performing the Digital Serology assay using a pair of QC index peptides under standard conditions or under conditions to mimic assay failure that might occur during screening. QC counts are expressed as the percentage of QC counts per total number of NGS reads. The percentage for each QC index in the pair is shown across multiple replicates.

Figure 3:
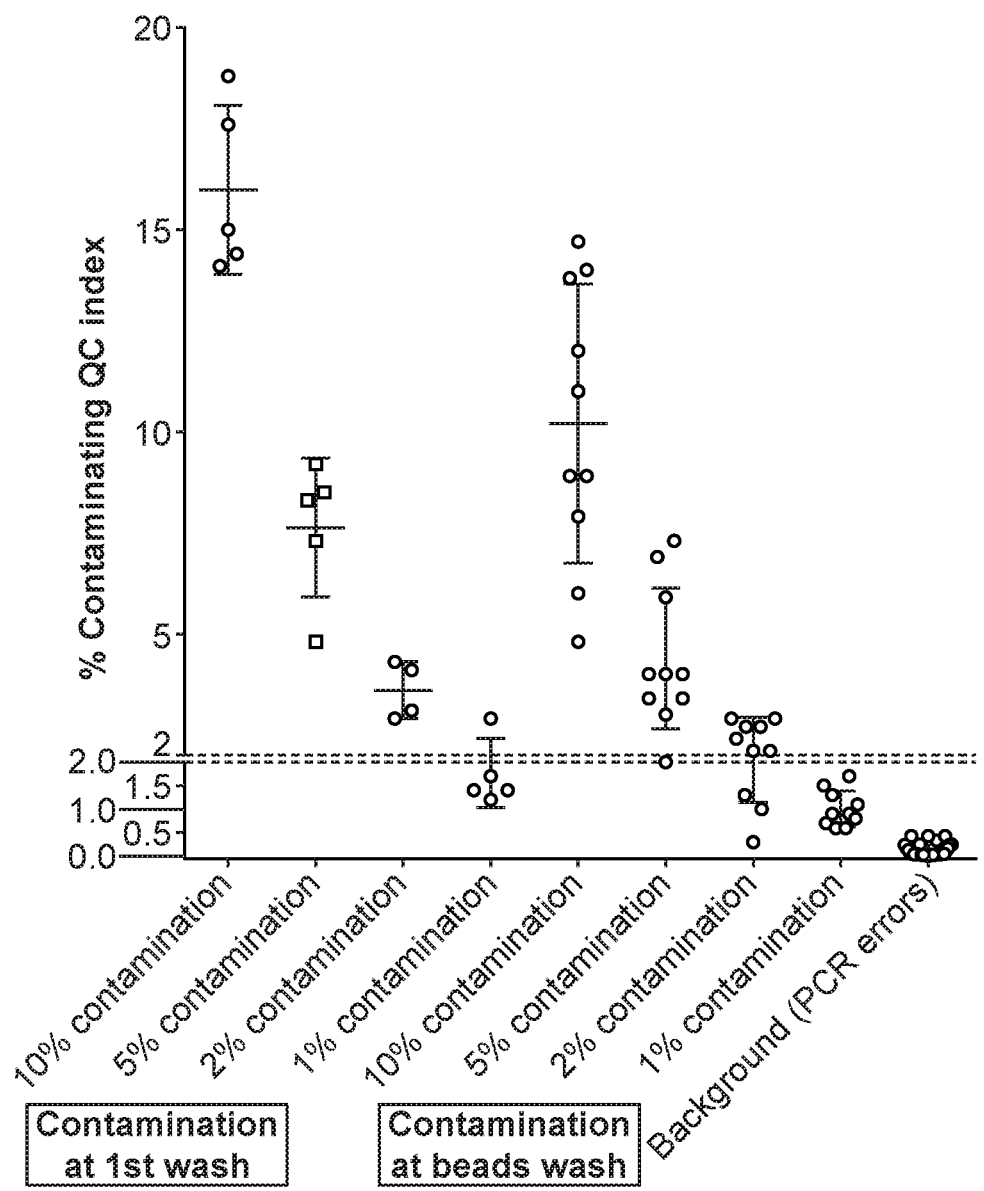

FIG. 3 demonstrates use of QC index peptides to determine sample contamination. Disease sera from patients with HIV and Tuberculosis were used to contaminate control sera at different levels of contamination and at different steps within the assay. Samples were processed using standard Digital Serology methods. The percent of contaminating QC index clones determined by NGS present in each sample relative to the correct index were calculated and are shown.

Figure 4A:
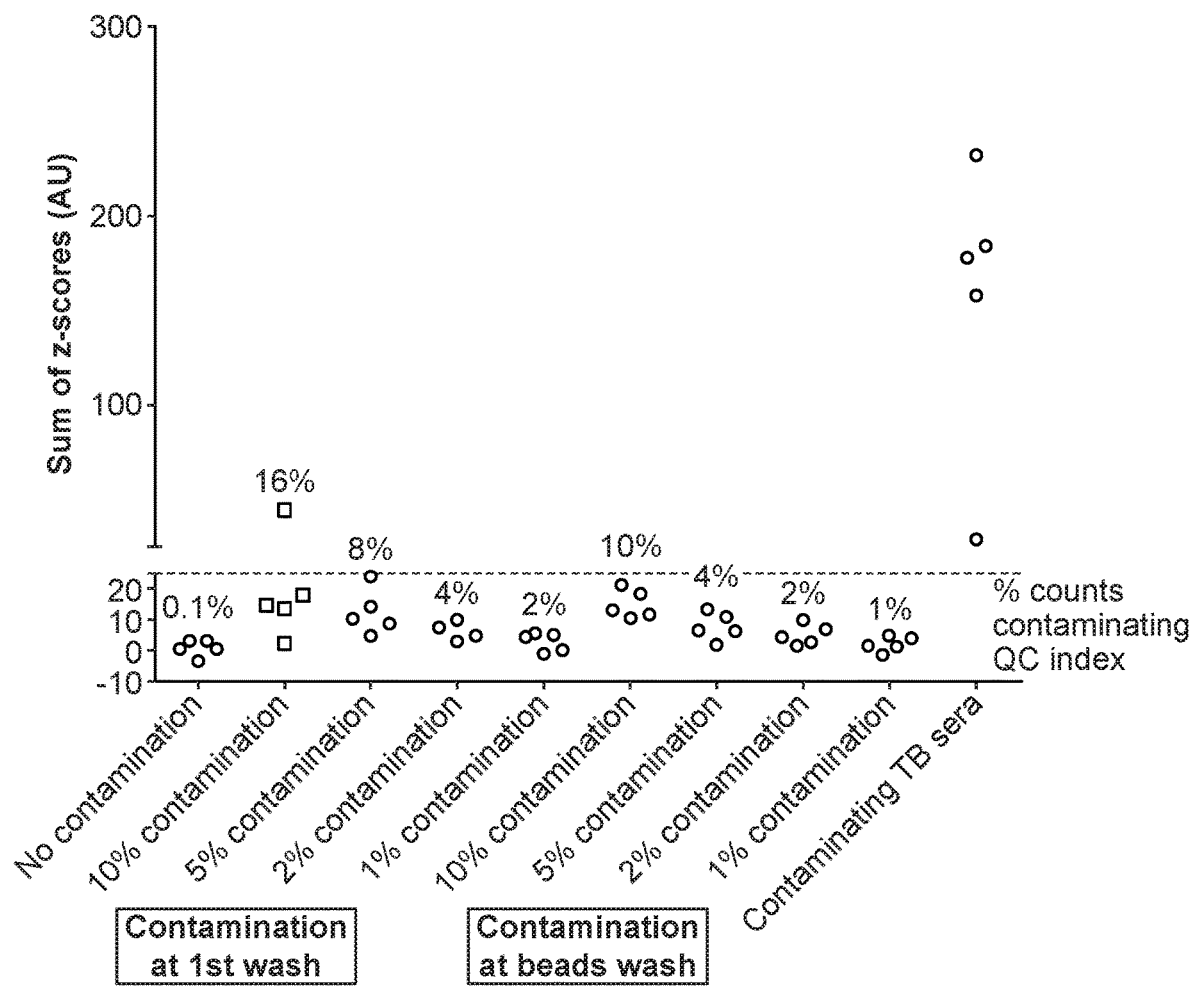
Figure 4B:
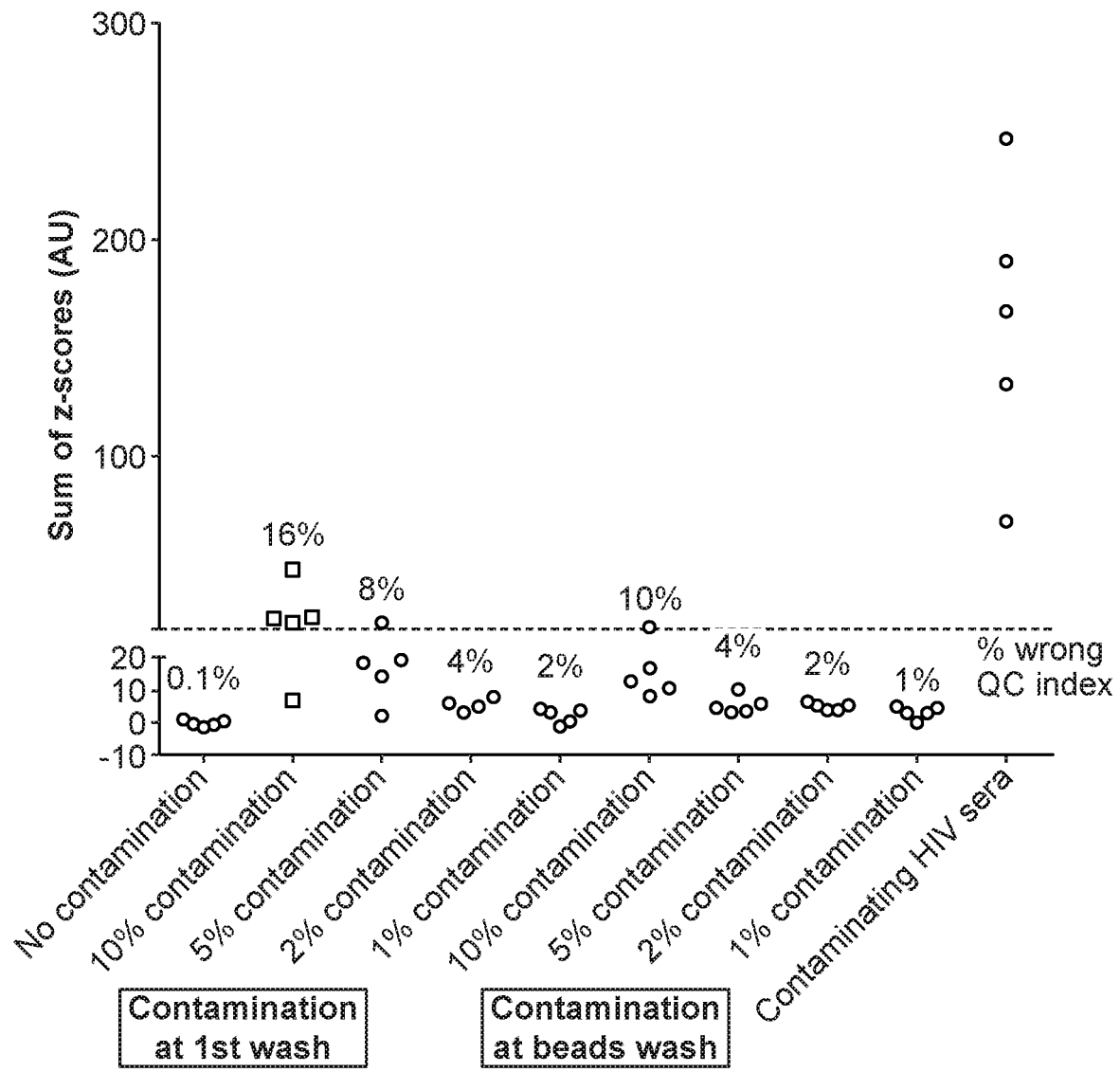

FIG. 4 demonstrates the impact of contamination on diagnostic accuracy. Control healthy sera was contaminated at different assay steps with various levels of sera known to be positive for tuberculosis (FIG. 4A) or HIV (FIG. 4B). Diagnostic scores for the specific disease that was the source of contamination were calculated for the motifs bound by antibodies in the contaminated healthy serum and are shown as the sum of z-scores. The dashed lines represent previously established disease specific motifs z-score diagnostic thresholds. The number of QC index counts specific for healthy sera as well as those specific for each of the disease sera were calculated and the percent of contaminating QC index clones shown above each sample.

FIG. 5 illustrates an exemplary QC index layout. Shown is a 96-well plate formatted with 10 unique QC clones (QC1-8, QC11, and QC12) arrayed by 8 unique clones (QC13-15 and QC19-23) to generate 80 unique QC pairs.

6. DETAILED DESCRIPTION

6.1. Definitions

Terms used in the claims and specification are defined as set forth below unless otherwise specified.

Unless specifically stated or otherwise apparent from context, as used herein the term "about" is understood as within a range of normal tolerance in the art, for example within 2 standard deviations of the mean. About can be understood as within 10%, 9%, 8%, 7%, 6%, 5%, 4%, 3%, 2%, 1%, 0.5%, 0.1%, 0.05%, or 0.01% of the stated value. Numerical values provided herein can sometimes be considered to be modified by the term about, where context makes clear that the ranges encompassed by the modification are consistent with operability of the invention and definiteness of the claims.

The term "enrichment" as used herein refers to the number of observations of a peptide, pattern, or motif within an epitope repertoire divided by the number expected within a random dataset of equivalent size. For example, in a hypothetical 9-mer peptide library (-XXXXXXXXX—), where X is any amino acid, the pattern QPXXPFX [ED] (SEQ ID NO:82) is expected to occur once in every 800,000 ((1aa/20aa)4x(2aa/20aa)x2) random sequences (aa=amino acid). If 4 million sequences were determined, then one would expect to observe five (5) occurrences (i.e., once in every 800,000 sequences). As an example, if the pattern was actually observed in 50 unique peptides sequences (i.e. 50 observations) in an epitope repertoire, then the pattern would be "enriched" by 10-fold versus random.

The term "threshold" as used herein refers to the magnitude or intensity that must be exceeded for a certain reaction, phenomenon, result, or condition to occur or be considered relevant. For example, the threshold can be a numerical value above which enrichment is considered relevant. The relevance can depend on context, e.g., it may refer to a positive, reactive or statistically significant relevance.

As used here, the terms "massively parallel signature sequencing" (MPSS) or "next generation sequencing" (NGS) and the like are used interchangeably to refer to high throughput nucleic acid sequencing (HTS) approaches. Platforms for NGS that rely on different sequencing technologies are commercially available from a number of vendors such as Pacific Biosciences, Ion Torrent from Thermo Fisher, 454 Life Sciences, Illumina, Inc. (e.g., MiSeq, NextSeq, HiSeq) and Oxford Nanopore. For a review of NGS technologies, see, e.g., van Dijk E L et al. Ten years of next-generation sequencing technology. Trends Genet. 2014 September; 30(9):418-26, herein incorporated by reference in its entirety for all purposes.

The term "surface display" as used herein refers to the presentation of heterologous peptides and proteins on an array surface, such as the outer surface of a biological particle such as a living cell, virus, or bacteriophage.

The term "disease" refers to an abnormal condition affecting the body of an organism. The term "disorder" refers to a functional abnormality or disturbance. The terms disease or disorder are used interchangeably herein unless otherwise noted or clear given the context in which the term is used. The terms disease and disorder may also be referred to collectively as a "condition."

The term "in situ" refers to processes that occur in a living cell growing separate from a living organism, e.g., growing in tissue culture.

The term "in vivo" refers to processes that occur in a living organism.

The term "mammal" as used herein includes both humans and non-humans and include but is not limited to humans, non-human primates, canines, felines, murines, bovines, equines, and porcines.

The term percent "identity," in the context of two or more nucleic acid or polypeptide sequences, refer to two or more sequences or subsequences that have a specified percentage of nucleotides or amino acid residues that are the same, when compared and aligned for maximum correspondence, as measured using one of the sequence comparison algorithms described below (e.g., BLASTP and BLASTN or other algorithms available to persons of skill) or by visual inspection. Depending on the application, the percent "identity" can exist over a region of the sequence being compared, e.g., over a functional domain, or, alternatively, exist over the full length of the two sequences to be compared.

For sequence comparison, typically one sequence acts as a reference sequence to which test sequences are compared. When using a sequence comparison algorithm, test and reference sequences are input into a computer, subsequence coordinates are designated, if necessary, and sequence algorithm program parameters are designated. The sequence comparison algorithm then calculates the percent sequence identity for the test sequence(s) relative to the reference sequence, based on the designated program parameters.

Optimal alignment of sequences for comparison can be conducted, e.g., by the local homology algorithm of Smith & Waterman, Adv. Appl. Math. 2:482 (1981), by the homology alignment algorithm of Needleman & Wunsch, J. Mol. Biol. 48:443 (1970), by the search for similarity method of Pearson & Lipman, Proc. Nat'l. Acad. Sci. USA 85:2444 (1988), by computerized implementations of these algorithms (GAP, BESTFIT, FASTA, and TFASTA in the Wisconsin Genetics Software Package, Genetics Computer Group, 575 Science Dr., Madison, Wis.), or by visual inspection (see generally Ausubel et al., infra).

One example of an algorithm that is suitable for determining percent sequence identity and sequence similarity is the BLAST algorithm, which is described in Altschul et al., J. Mol. Biol. 215:403-410 (1990). Software for performing BLAST analyses is publicly available through the National Center for Biotechnology Information (www.ncbi.nlm.nih.gov/).

The term "sufficient amount" means an amount sufficient to produce a desired effect.

The term "therapeutically effective amount" is an amount that is effective to ameliorate a symptom of a disease. In some contexts, a therapeutically effective amount can be a "prophylactically effective amount" as prophylaxis can be considered therapy, provided such interpretation does not adversely impact any determination of the validity of any claim for any reason.

It must be noted that, as used in the specification and the appended claims, the singular forms "a." "an," and "the" include plural referents unless the context clearly dictates otherwise.

6.2. Peptide Library with Quality Control Peptides

As described herein, peptide expression library compositions are provided. In a first aspect, the library composition comprises a library of nucleic acid sequences encoding a library of peptides and one or more control vectors. The one or more control vectors comprise a nucleic acid sequence encoding a control binding target of a control binding molecule, wherein the control binding target is identical for each of the control vectors, and a unique nucleic acid sequence, wherein the unique nucleic acid sequence is specific for each of the control vectors. The control binding target is optionally a defined peptide sequence, and the unique nucleic acid sequence optionally encodes a unique peptide sequence expressed a part of the defined peptide sequence.

In a series of embodiments, the composition further comprises two or more array surfaces, wherein each of the array surfaces is configured to display either one or more copies of one of the peptides of the library of peptides, or one or more copies of the control binding target expressed by one of the control vectors.

6.2.1. Peptide Libraries

As used herein, a "library of peptides" or a "peptide library" refers to a collection of a peptide fragments typically used for screening purposes. The terms "peptide," "polypeptide," "amino acid sequence," "peptide sequence," and "protein" are used interchangeably to refer to two or more amino acids linked together and imply no particular length. Amino acids and peptides can be naturally occurring or synthetic (e.g., unnatural amino acids or amino acid analogs). Amino acids and peptides can also comprise, or be further modified to comprise, reactive groups, such as reactive groups for attaching amino acids or peptides to solid substrates, reactive groups for labeling amino acids or peptides, or reactive groups for attaching other moieties of interest to amino acids or peptides. Reactive groups include, but are not limited to, chemically-reactive groups such as reactive thiols (e.g., maleimide based reactive groups), reactive amines (e.g., N-hydroxysuccinimide based reactive groups), "click chemistry" groups (e.g., reactive alkyne groups), and aldehydes bearing formylglycine (FGly).

In general, a peptide library contains a large variety of unique peptides. For example, the diversity of the library (sometimes referred to as "complexity" of the library) can be more than $10^4$, more than $10^5$, more than $10^6$, more than $10^7$, more than $10^8$, more than $10^9$, more than $10^{10}$, or more than $10^{11}$ unique peptides. The library can be a random peptide library where the amino acid sequences are unbiased. A particular embodiment of a random/unbiased library is one constructed to represent all possible amino acid sequences of designated length(s).

A peptide library can also be a non-random library where the amino acid sequences are biased in their representation. For example, a library can be biased to represent, over represent, predominantly represent, or only represent amino acid sequences characteristic of a particular feature, such as epitopes or antigens associated with a particular disease (e.g., a bacterial infection, a viral infection, a parasitic infection, an autoimmune disorder, cancer, allergies etc.), condition, species (e.g., mammal, human, bacteria, virus etc.), protein, class of proteins, protein motif (e.g., phosphorylation motifs, binding motifs, protein domains, etc.), amino acid property (e.g., hydrophobic, hydrophilic, acidic, basic, or steric amino acid properties), or any other subset of amino acid sequences that is rationally designed. A library can be biased to also avoid certain amino acid sequences or motifs.

A peptide library can also combine the features of a non-random and random peptide library. For example, one or more select positions within an amino acid sequence may be a constant amino acid and other positions within the sequence may be fully random or biased based on other properties. In other examples, one or more select positions within an amino acid sequence may be selected from a defined subset of amino acids. One skilled in the art will appreciate that the various biases described can combined to achieve a desired purpose of the peptide library, such as a targeted screen.

Typically, peptides in a library can also all fall within a range of lengths. For example, the peptides in a library may be different lengths, but all fall within a defined range of lengths. The selected range can be any length useful for the present invention, such as any length suitable for displaying an epitope sequence capable of recognition by a binding molecule. The peptides in a library can be at least 5, 6, 7, 8, 9, 10, 11, 12, 13, 14, 15, 16, 17, 18, 19, or 20 amino acids in length. The peptides in a library can also be 5-30, 5-25, 5-20, 5-15, 5-10, 10-30, 10-25, 10-20, or 10-15 amino acids in length. The peptides in a library can also be 7-14, 8-14, 9-14, 10-14, 11-14, 12-14, 7-13, 8-13, 9-13, 10-13, 11-13, 12-13, 7-12, 8-12, 9-12, 10-12, 11-12, 7-11, 8-11, 9-11, or amino acids in length. If desired, the peptides in the library can also be greater than 30, greater than 40, greater than 50, greater than 75, greater than 100, greater than 200, or greater than 300 amino acids in length.

Peptides in a library can also be an identical defined length, i.e., all the peptides in the library have the same number of amino acids. The defined length can be any length useful for the present invention, such as any length suitable for displaying an epitope sequence capable of recognition by a binding molecule. The defined length can be 5, 6, 7, 8, 9, 10, 11, 12, 13, 14, 15, 16, 17, 18, 19, or 20 amino acids in length.

A peptide expression library refers to a collection of nucleic acid sequences capable of expressing a peptide library. The nucleic acid sequences can be constructed to achieve a desired library property including those described above, such as peptide diversity, peptide randomization or biasing, and/or peptide length. Any suitable nucleic acid allowing expression of the peptides of interest may be used. In general, the nucleic acid will be a vector. As used herein, a "vector" refers to nucleic acid construct capable of directing the expression of a gene of interest, typically in a host organism, such as a bacterial cell, mammalian cell, or bacteriophage. A vector typically contains the appropriate transcriptional and translational regulatory nucleotide sequences recognized by the desired host for peptide expression, such as promoter sequences. A promoter sequence can be a constitutive promoter. A promoter sequence can be an inducible promoter, where transcription of the encoded sequences is induced by addition of an analyte, chemical, or other molecule, such as a Tet-on system. A variation of an inducible promoter system is a system where transcription is actively repressed, and addition of an analyte, chemical, or other molecule removes the repression, such as addition of arabinose for an arabinose operon promoter or a Tet-off system. A vector can also include elements that facilitate vector construction and production, such as restriction sites, sequences that direct vector replication, drug selection genes or other selectable markers, and any other elements useful for cloning and library production. A typical vector can be a double stranded DNA plasmid in which the nucleic acid sequences encoding the desired peptides is inserted using standard cloning techniques in a location and orientation capable of directing peptide expression. Other vectors include, but are not limited to, nucleic acid constructs useful for in vitro transcription and translation, linear nucleic acid constructs, and single-stranded DNA or RNA nucleic acid constructs.

In general, the number of copies of a specific nucleic acid sequence for each of the candidate peptides is present at a roughly equivalent number, though some variation in number may occur due to probability. A typical peptide expression library can contain more than one copy of a specific nucleic acid sequence (e.g., multiple copies of the same vector). However, in examples where a plurality of samples each contain members of the peptide expression library, the absolute number of each of the candidate peptides may not be equivalent between samples. For example, zero or one copy of a specific nucleic acid sequence can be present in a given sample while one or more copies may be present in another given sample. While the number of copies of a specific nucleic acid sequence need not be identical to the number of copies of other specific nucleic acid sequences, it is generally assumed that about the same number of sequences are present for each of the candidate peptides.

Peptide expression libraries include, but are not limited to, bacterial expression libraries, yeast expression libraries, bacteriophage expression libraries, and mammalian expression libraries. Particular peptide libraries and peptide expression libraries useful for the present invention are described in more detail in issued U.S. Pat. No. 7,256,038, issued U.S. Pat. No. 8,293,685, issued U.S. Pat. No. 7,612,019, issued U.S. Pat. No. 8,361,933, issued U.S. Pat. No. 9,134,309, issued U.S. Pat. No. 9,062,107, issued U.S. Pat. No. 9,695,415, and U.S. published application US20160032279, each herein incorporated by reference for all it teaches.

6.2.2. Control Binding Targets

As used herein, a "binding target" refers to any molecule that may be specifically and selectively bound a binding molecule. As used herein, a "control binding target" refers to a defined binding target that is selectively expressed by a control vector or subset of control vectors. In a specific example, a binding target is a defined peptide sequence, such as an epitope sequence. As used herein, an "epitope" or "epitope sequence" refers to the specific portion of an antigen typically bound by an antibody or T cell receptor. In general, the defined peptides described herein refer to well characterized epitope sequences or "tags" that are recognized by antibodies also well characterized in the field. Examples of well characterized epitopes and their respective antibodies include, but are not limited to, FLAG (DYKDDDDK, SEQ ID NO:3), Myc (EQKLISEEDL, SEQ ID NO:4), HA (YPYDVPDYA, SEQ ID NO:5), His (HHHHHH, SEQ ID NO:6), 3X-FLAG (DYKDHDGDYKDHDIDYKDDDDK, SEQ ID NO:7), V5 (GKPIPNPLLGLDST, SEQ ID NO:8), and VSV-G (YTDIEMNRLGK, SEQ ID NO:9). A binding target or epitope can also be selected based on specific screening considerations. For example, for assays involving screening human serum for antibody binding, epitopes derived from human pathogens (e.g., the HA-tag derived from human influenza) can be avoided for use as control binding targets to reduce the potential for serum antibodies binding to the epitope. Other epitopes generally encountered in a population can be avoided for use as control binding targets, such as epitopes present above a specified frequency in the population, such as those epitopes present at a frequency greater than 1 in 1000, greater than 1 in $10^4$, greater than 1 in $10^5$, or greater than 1 in $10^6$. Other epitopes considered to be generally encountered in a population can also include those antibody epitopes present in a database of antibody repertoires, including databases of human antibody repertoires.

In other examples, binding targets are molecules recognized by other molecules aside from antibodies. Examples of such binding molecules include, but are not limited to, aptamers, peptoids, and affibodies, as described in more detail in Perret and Boschetti (*Biochimie*. February 2018, Vol 145:98-112), herein incorporated by reference for all it teaches.

In certain embodiments, the peptide expression library composition can have one or more second control vectors that contain a nucleic acid encoding a second control binding target. For example, in a non-limiting illustration, one subset of control vectors expresses a first binding target, such as a Flag epitope, while another subset (the "second" control vectors) expresses a second binding target, such as a Myc epitope.

6.2.2.1. Control Binding Molecules

As used herein, "control binding molecules" refer to those molecules that specifically and selectively bind the control binding target(s). In a typical example, a control binding molecule is an antibody. The antibody can be a monoclonal antibody, which are typically produced from cultured antibody-producing cell lines, or a polyclonal antibody, which are typically produced by collecting the antibody containing serum of an animal immunized with the antigen or epitope of interest, or fragment thereof. Antibodies specific for the well characterized epitope tags described above are all commercially available. Antibodies can also refer to antibody fragments or antibody formats including, but not limited to, full-length antibodies, Fab fragments, Fvs, scFvs, tandem scFvs, Diabodies, scDiabodies, DARTs, tandAbs, minibodies, camelid VHH, and other antibody fragments or formats known to those skilled in the art. Exemplary antibody and antibody fragment formats are described in detail in Brinkmann et al. (*MABS*. 2017, Vol. 9, No. 2, 182-212), herein incorporated by reference for all that it teaches.

In other examples, the control binding molecule(s) can refer to binding molecules other than antibodies including, but not limited to, aptamers, peptoids, and affibodies. One skilled in the art can also recognize that the control binding molecule can be any binding molecule that specifically and selectively binds the selected control binding target(s).

6.2.2.2. Capture Entities

In one example of the invention, the control binding molecule described above is bound to or capable of being bound to a capture entity. As used herein, a "capture entity" refers to any entity useful for capturing or isolating a binding molecule. The binding molecule can be the "control" binding molecule described above, as well as other binding molecules present in a sample, such as serum antibodies in a patient's sample (see Section 6.3.1).

In a typical example, the capture entity comprises a solid support. As described herein, "solid support" refers to a material to which other entities can be attached (i.e., immobilized). Solid supports, also referred to as "carriers or substrates," are described in more detail in international application WO 2009/011572. Solid supports can include, but are not limited to, a plurality of beads (also referred to as microbeads, microparticles, nanoparticles, or nanobeads) or planar surface (e.g., a multi-well plate). Examples of beads include, but are not limited to, agarose beads, polystyrene beads, magnetic beads (e.g., Dynabeads™ThermoFisher or Pierce), polymers (e.g., dextran), synthetic polymers (e.g., Sepharose™), or any other material suitable for capturing binding molecules. The capture entities (e.g., the solid supports) can also be modified or functionalized to bind and capture (i.e., immobilize) binding molecules. Such modifications can be attaching to or coating the surface of a capture entity with a "binding moiety" that binds the binding molecules. Examples include binding moieties that specifically bind antibodies, such as Protein A, Protein G, Protein A/G, Protein L, or an anti-immunoglobulin antibody. Other examples of modifications include chemical modifications that allow formation of covalent bonds with proteins (e.g., activated aldehyde groups) and modifications that specifically pair with a cognate modification of a binding molecule (e.g., biotin-streptavidin pairs, disulfide linkages, polyhistidine-nickel, or "click-chemistry" modifications such as azido-alkynyl pairs). As a non-limiting illustration, a binding molecule can be modified to contain a biotin moiety (i.e., biotinylated) and a capture entity can be modified to contain streptavidin on its surface.

Capture entities can also possess further modifications or functionalized properties that aid in the methods and processes of capturing and isolating binding molecules. As non-limiting illustrations, capture entities can have magnetic properties that allow for magnetic isolation, or capture entities can have fluorescent molecules attached that allow, for example, fluorescence-activated cell sorting (FACS). Other properties include the ability to remove (e.g., elute or cleave off) captured binding molecules and/or their respective binding target if desired.

In the methods describe herein, where a binding molecule is used to bind a binding target, the binding molecule can either be immobilized on a capture entity prior to the binding molecule binding its target (e.g., prior to contacting or mixing the peptide library with the binding molecule), or the binding molecule can be immobilized on a capture entity subsequent to the binding molecule binding its target.

As a non-limiting illustration of a capture entity, a magnetic bead is functionalized with Protein A/G (e.g., Pierce). The Protein A/G bead is subsequently used to capture antibodies bound to their respective epitope targets.

6.2.3. Unique Nucleic Acid Sequences

As used herein, a "unique nucleic acid sequence" refers to a defined unique nucleic acid sequence specific for a given control vector expressing a control binding target. In general, while more than one control vector within a peptide expression library can express the same control binding target, a defined control vector (including multiple copies thereof) contains an identical unique nucleic acid sequence. The peptide expression library can contain one, two, three or more specific control vectors (e.g., one, two, three or more defined subsets where each subset contains an identical unique nucleic acid sequence).

The unique nucleic acid sequences can be at least 4, 5, 6, 7, 8, 9, 10, 11, 12, 13, 14, 15, 16, 17, 18, 19, 20, 21, 22, 23, 24, 25, 26, 27, 28, 29, or 30 nucleotides in length. In examples where the peptide expression library contains two or more control vectors, each unique nucleic acid sequences can be an identical defined length, such as 4, 5, 6, 7, 8, 9, 10, 11, 12, 13, 14, 15, 16, 17, 18, 19, 20, 21, 22, 23, 24, 25, 26, 27, 28, 29, or 30 nucleotides in length. In examples where the peptide expression library contains two or more control vectors, each of the unique nucleic acid sequences can differ by at least 2, at least 3, at least 4, at least 5, at least 6, at least 7, at least 8, at least 9, at least 10-15, at least 15-20, or at least 20-30 nucleotides.

Unique nucleic acid sequences can be in a portion of the control vector such that it is not transcribed but is in a region constructed to allow amplification for downstream processes, such as NGS. As described in greater detail in Section 6.2.3.2, unique nucleic acid sequences can encode a unique peptide sequence expressed a part of the defined peptide sequence.

6.2.3.1. Control Vector Ratio

In general, the percentage of the peptide expression library composition made up by the one or more control vectors can be an important aspect to control in the current invention. Controlling the ratio of control vector to candidate sequences within the library can be used to establish quality control thresholds, such as the expected percentage of sequencing reads determined by NGS or the total number of sequencing reads determined by NGS. The one or more control vectors can be added to peptide expression library such that the total number of nucleic acid sequences in the library of nucleic acid sequences (i.e., the total number of candidate library peptide sequences) and the total number of each of the one or more control vectors is at a defined ratio. The defined ratio of the total number of nucleic acid sequences in the library of nucleic acid sequences to the total number of each of the one or more control vectors can be between $1 \times 10^4$ and $1 \times 10^8$. The defined ratio can be about $1 \times 10^4$, about $1 \times 10^5$, about $1 \times 10^6$, about $1 \times 10^7$, or about $1 \times 10^8$. The defined ratio can be at least $1 \times 10^4$, at least $5 \times 10^4$, at least $7.5 \times 10^4$, or at least $1 \times 10^5$. The defined ratio can be at least $1 \times 10^5$, at least $1 \times 10^6$, at least $1 \times 10^7$, or at least $1 \times 10^8$.

The one or more control vectors can be added to peptide expression library such that the total number of nucleic acid sequences in the library is about $1 \times 10^4$, about $1 \times 10^5$, about $1 \times 10^6$, about $1 \times 10^7$, or about $1 \times 10^8$. The one or more control vectors can be added to peptide expression library such that the total number of nucleic acid sequences in the library is at least $1 \times 10^4$, at least $1 \times 10^5$, at least $1 \times 10^6$, at least $1 \times 10^7$, or at least $1 \times 10^8$.

6.2.3.2. Unique Peptide Sequences

Unique nucleic acid sequences can encode a unique peptide sequence expressed a part of the defined peptide sequence. The unique peptide sequences can be at least 3, 4, 5, 6, 7, 8, 9, 10, 11, 12, 13, 14, 15, 16, 17, 18, 19, or 20 or more amino acids in length. In examples where the peptide expression library contains two or more control vectors, each unique peptide sequences can be an identical defined length, such as 3, 4, 5, 6, 7, 8, 9, 10, 11, 12, 13, 14, 15, 16, 17, 18, 19, or 20 or more amino acids in length. The unique peptide sequences can be 4 amino acids in length. Defined peptide sequences and unique peptide sequences can be immediately adjacent to each other or separated by an additional peptide sequence, and can be N-terminal or C-terminal of the unique peptide sequence.

Composition of the defined peptide sequence, when expressed, can be important to control. For example, in examples where the peptide expression library contains two or more control vectors, the various defined peptide sequence can be constructed to limit the potential effect of amino acid composition on overall expression that may lead to artifacts. In a non-limiting illustrative example, each of the defined peptides each are composed overall of the same amino acids but the order of the amino acids is unique for each defined peptide. Thus, any potential expression bias due to presence of a particular amino acid will be minimized. In other examples, at least one amino acid in the overall composition is different but is substituted for an amino acid of the same class, e.g., hydrophobic, hydrophilic, etc.

6.2.4. Library Array

In a series of embodiments, a composition can be composed of two or more of the peptide expression library compositions described above. The two or more peptide expression library compositions can each be contained in a separate container, such as a well in a multi-well plate, a microcentrifuge tube, a test tube, a tube, and a PCR tube. Each of the separate containers can comprise the same library of nucleic acid sequences encoding the library of peptides but where each container contains a different control vector (i.e., a control vector with a unique nucleic acid sequence). In another example, each of the separate containers can comprise the same library of nucleic acid sequences encoding the library of peptides but where each container contains a different combination of control vectors. e.g., where a given container may share one or more of the control vectors in common with another container, but the exact combination of control vectors is unique to that given container. The combination of control vectors can also be such that a given container does not share any of the control vectors with another container.

In a particular embodiment, a container can be a well within a multi-well plate, e.g., a 96-well plate, and the compositions are arranged such that each of the peptide expression library compositions contains at least one control vector that is different than those in an adjacent well. In another particular embodiment, a container can be a well within a multi-well plate, each of the peptide expression library compositions contains at least two vector controls, and the compositions are arranged such that each adjacent well does not share a control vector in common.

The collection of peptide expression library compositions can be 2, 3, 4, 5, 6, 7, 8, 9, 10-15, 16-24, 24-48, 48-96, or 96-384 peptide expression library compositions. The collection of peptide expression library compositions can be at least 10, at least 20, at least 50, at least 100, at least 200, at least 300, at least 500, at least 1000, or at least 2000 expression library compositions.

6.2.5. Array Surfaces

As used herein, "array surfaces" refers to any surface that can be configured to display (i.e., present) binding targets in a manner suitable for recognition by their respective binding molecules.

Array surfaces can be biological surfaces (e.g., the outer membrane surface of cell). Biological entities that can be used include, but are not limited to, a mammalian cell, a yeast, a bacteria, a virus, and a bacteriophage. The members of the library of peptides (e.g., candidate peptides) and/or the control binding targets can be engineered to be expressed on the surface of a cell, such as constructing the library of nucleic acid sequences encoding the library of peptides or the nucleic acid sequences encoding the control binding targets to also encode a cell surface display peptide sequence configured to be expressed as part of the peptide and capable of directing the peptides for display on the biological entity surface. Illustrative non-limiting examples of *E. coli* cell surface displayed libraries are described in greater detail in in issued U.S. Pat. No. 7,256,038, issued U.S. Pat. No. 8,293,685, issued U.S. Pat. No. 7,612,019, issued U.S. Pat. No. 8,361,933, issued U.S. Pat. No. 9,134,309, issued U.S. Pat. No. 9,062,107, issued U.S. Pat. No. 9,695,415, and U.S. published application US20160032279, each herein incorporated by reference for all it teaches.

Array surfaces can include solid supports, as described in Section 6.2.2.2. Solid supports can be have proteins, nucleic acids, or both attached to their surface and can be adapted for use in the present invention. Methods of attaching proteins and nucleic acids are known to those skilled in the art and include, but are not limited to, use of chemically reactive groups such as reactive thiols (e.g., maleimide based reactive groups), reactive amines (e.g., N-hydroxysuccinimide based reactive groups), "click chemistry" groups (e.g., reactive alkyne groups), aldehydes bearing formylglycine (FGly) and other cognate modifications (e.g., biotin-streptavidin pairs, disulfide linkages, polyhistidine-nickel).

In general, the array surface used will be the same for both the library of peptides and the control binding targets. The array surfaces used for the library of peptides can be different from the control binding targets, if desired.

6.3. Method of Assay Quality Control

Also provided for herein are methods for assay quality control. In a first aspect, the method comprises a) providing a sample known or suspected to have specimen binding molecules, b) providing any of the peptide expression library compositions described in section 6.2, wherein the library of peptides is expressed, the control binding target is expressed, and wherein each of the array surfaces displays one or more copies of: 1) one of the peptides of the library of peptides, or 2) the control binding target, and wherein the unique nucleic acid sequences of the one or more control vectors is specific for the sample; c) providing the control binding molecule, and d) contacting the sample with the peptide expression library composition and the control binding molecule.

In further aspects, the method can also comprise the additional steps of e) isolating the specimen binding molecules and the control binding molecules bound to peptides bound to peptides, f) determining: 1) the unique nucleic acid sequences specific for each of the control vectors encoding the control binding targets bound by the isolated control binding molecules, and 2) unique nucleic acid sequences associated with one or more control vectors that are not specific for the sample, optionally wherein the unique nucleic acid sequences not specific for the sample express the control binding target bound by the isolated control binding molecules, and g) assessing or having assessed from step (f) whether the determined nucleic acid sequences meets a quality control standard.

6.3.1. Samples

As used herein, a "sample" refers to any material known to contain or suspected to contain specimen binding molecules (e.g., antibodies). In general, the sample will be a liquid. The sample can be a material that originated as a liquid or can be material processed to be in liquid form. The sample can be the material directly isolated from a source (i.e., untreated) or it can be further processed for use in the method (e.g., diluted, filtered, cell depleted, particulate depleted, assayed, preserved, or other otherwise pre-processed). Samples include, but are not limited to, serum, blood, saliva, urine, tissue, tissue homogenates, stool, spinal fluid, and lysate derived from animal sources. The sample can include a mixture of different source materials. A sample can be a bodily fluid isolated from any animal that produces or suspected to produce the binding molecule of interest. The animal can be known or suspected of having a disease. The animal can also be known or suspected of having binding molecules that bind antigens or epitopes associated with the disease. In an illustrative non-limiting example, the sample can be processed serum from human suspected to have a specific disease and suspected to produce antibodies that bind epitopes that correlate with the disease. Diseases include, but are not limited to, a bacterial infection, a viral infection, a parasitic infection, an autoimmune disorder, cancer, and an allergy.

6.3.2. Assay Methods

As used herein, "contacting" refers to any method of bringing the specimen binding molecules and the control binding molecules in proximity to and under conditions sufficient for binding to their respective binding targets. The contacting of the different components can be performed in any suitable order. For example, the peptide expression library composition and the control binding molecule can be contacted prior to contacting either with the sample. In another example, the sample and the control binding molecule can be contacted prior to contacting either with the peptide expression library composition.

Contacting can include mixing all the compositions together. Mixing can be performed in a container, such as a well in a multi-well plate, a microcentrifuge tube, a test tube, a tube, and a PCR tube. Mixing can include rotating, incubating, pipetting, inverting, vortexing, shaking, or otherwise mechanically disturbing components.

Isolation steps used herein can be any method useful for retrieving specimen and control binding molecules. Isolation can involve the use of capture entities, described in more detail in Section 6.2.2.2. Isolation methods include, but are not limited to magnetic isolation, bead centrifugation, resin centrifugation, and FACS. A particular isolation method can be selected based on the properties of a capture entity, if used, for example magnetic isolation of magnetic beads or FACS isolation of fluorescent beads.

Determining steps, as used herein, in general can use any method for sequencing and/or quantifying nucleic acid, such as next generation sequencing (NGS) or quantitative polymerase chain reaction (qPCR). Examples of NGS technologies include massively parallel sequencing techniques and platforms, such as Illumina HiSeq or MiSeq, Thermo PGM or Proton, the Pac Bio RS II or Sequel, Qiagen's Gene Reader, and the Oxford Nanopore MinION. Additional similar current massively parallel sequencing technologies can be used, as well as future generations of these technologies. In some embodiments, the determining step contains the steps of 1) purifying the nucleotide from the biological entity; 2) amplifying the unique nucleic acid sequences and optionally the nucleic acid sequences encoding a peptide bound by the isolated specimen binding molecules; and 2) sequencing the amplified nucleotides. The nucleic acid to be sequenced can also be further modified or processed to facilitate sequencing. For example, nucleic acid can be modified for multiplexed high-throughput sequencing of multiple samples simultaneously, such as adding a sample identifying nucleic acid sequence unique to the sample to terminus of the amplified nucleotides during the amplification step.

Various nucleic acid sequences (e.g., sequences encoding a library of peptides, sequences encoding a control binding target, unique nucleic acid sequences) can be differentiated from each other during the determining step(s). Differentiating various nucleic acid sequences includes differentiating portions of nucleic acid sequences, such as differentiating the different sequences in a vector (e.g., differentiating a nucleic acid sequence encoding a binding target from unique nucleic acid sequence). Sequences can be differentiated based on specific characteristics, such as position within a sequence, identity of adjacent sequences, known identity of sequences, or combinations thereof. Sequence alignment algorithms, such as those known in the art, can be used to identify, quantify, and differentiate the different sequences.

6.3.3. Quality Control Assessment

Following sequencing a sample, the results can be used to assess the quality or validity of the assay, such as the validity of the data obtained for a library screen. The identity and quantity of the isolated unique nucleic acid sequences can be used to assess whether the assay meets a quality control standard. The identity and quantity of the isolated nucleic acids that encode candidate peptides in a peptide expression library can also be used in the assessment.

A particular advantage of the methods described herein is the assessment can be used to establish whether a potential error occurred during the method. Examples of errors include, but are not limited to, improper expression of the candidate peptides from the peptide expression library (e.g., reduced expression of the candidate peptides), improper expression of the control binding target, or improper binding conditions for any of the binding molecule/target pairs, improper binding of the control binding target by the control binding molecule (e.g., use of the wrong control binding molecule), improper isolation of the binding molecules (e.g., use of the wrong capture entities), absence of a component (e.g., absence of the sample, peptide library, control vector, control binding molecule, or capture entity), improper quantities of a component (e.g., improper concentration of the peptide library, control vector, control binding molecule, or capture entities), improper sample dilution, sample contamination, or combinations thereof.

The assessment can involve the use of a computer. In general, a computer is adapted to execute a computer program for providing results, for example the results of determining nucleic acid sequences such as those sequences produced during a sequencing step or the results of an assessment step providing if the assay meets a quality control standard. Generally, the steps of determining the nucleic acid sequences and determining the results of the assessment step involve such a large number of computations, particularly given the number of sequences generally under consideration, that they are carried out by a computer system in order to be completed in a reasonable amount of time. They cannot be practically carried out by the human mind or by pen and paper alone. A computer can include at least one processor coupled to a chipset. Also coupled to the chipset can be a memory device, a memory controller hub, an input/output (I/O) controller hub, and/or a graphics adaptor. Various embodiments of the invention may be implemented as a computer program instructions stored in a non-transitory computer readable storage medium for execution by a processor of a computer system. The instructions define functions of the embodiments (including the methods described herein). Illustrative computer-readable storage media include, but are not limited to: (i) non-writable storage media (e.g., read-only memory devices within a computer such as CD-ROM disks readable by a CD-ROM drive, flash memory, ROM chips or any type of solid-state non-volatile semiconductor memory) on which information is permanently stored; and (ii) writable storage media (e.g., floppy disks within a diskette drive or hard-disk drive or any type of solid-state random-access semiconductor memory) on which alterable information is stored. A computer can include a means for programming the computer (i.e., providing computer program instructions), such as providing sequence alignment software or quality control assessment software. A computer can include a means for inputting information, such as sequences, including, but not limited to, a keyboard, a mouse, a touch-screen interface, or combinations thereof. A computer can include a means to display information and images, such as a graphics adaptor and display. A computer can include means to connect to other computers (e.g., computer networks), such as a network adaptor. Some portions of the description herein describe the embodiments in terms of algorithms and symbolic representations of operations on information. These algorithmic descriptions and representations are commonly used by those skilled in the data processing arts to convey the substance of their work effectively to others skilled in the art. These operations, while described functionally, computationally, or logically, are understood to be implemented by computer programs, equivalent electrical circuits, or the like. The described operations and their associated modules may be embodied in software, firmware, hardware, or any combinations thereof. A quality control standard can be a ratio or percentage of unique peptide sequences specific present in a sample. The ratio or percentage can be relative to unique peptide sequences that are not specific to a sample (e.g., present as a result of sample contamination). The ratio or percentage can also be relative to the total number of any subset of nucleic acid sequences useful for establishing a quality control standard, such as sequences encoding a library of peptides, sequences encoding a control binding target, unique nucleic acid sequences, or combinations thereof.

A particular advantage of the methods described herein is that the assessment can be used to establish whether contamination occurred between samples assayed, such as samples assayed in a multiplexed array. In one example, the determining step, such as NGS to identify and quantify all unique nucleic acid sequences, can be used to calculate a percentage of the unique nucleic acid sequences specific for the sample (i.e., the sequence(s) assigned to a given sample) present relative to a total number of unique nucleic acid sequences, wherein the total number comprises the number of the unique nucleic acid sequences specific for the sample and the number of the unique nucleic acid sequences not specific for the sample (i.e., the quantity of all unique nucleic acid sequences regardless of sample assignment). Assessing whether a method meets a contamination threshold value can be used as part of the overall assessment of the assay meeting a quality control standard. Contamination thresholds can be the values for which the percentage of the unique nucleic acid sequences specific for the sample indicates there is either zero, minimal, or negligible sources of unique nucleic acid sequences not specific for the sample (e.g., contamination). Negligible sources of contamination include contamination levels at which an assay is still considered diagnostically valid even in the presence of detectable contamination. Accordingly, a percentage that falls below an established contamination threshold can indicate contamination (or non-negligible levels of contamination) between samples, or other potential sources of error in the method, and invalidate the sample. The contamination threshold can be between 90-100%, between 92-100%, between 95-100%, between 96-100%, or between 98-100%. The contamination threshold can be about 90%, about 92%, about 95%, about 96%, about 97%, about 98%, or about 99%. The contamination threshold can be at least 90%, at least 92%, at least 95%, at least 96%, at least 97%, at least 98%, or at least 99%. The contamination threshold can be at least 98%. The contamination threshold can be 98%. The contamination threshold can be at least 99%. The contamination threshold can be 99%.

Another particular advantage of the methods described herein is that the assessment can be used to establish whether an error occurred during analysis of the samples, such as a technical error in the biopanning or NGS methods described herein. The determining step, such as NGS to identify and quantify all unique nucleic acid sequences, can be used to calculate a percentage of the unique nucleic acid sequences specific for the sample relative to a total number of nucleic acid sequences, the total number comprising the number of the unique nucleic acid sequences specific and not specific the sample and the number of nucleic acid sequences encoding the peptides in the library of peptides (e.g., a QC-clone-reads/total-reads ratio). Assessing whether a method meets an error threshold value can be used as part of the overall assessment of the assay meeting a quality control standard. Error thresholds are the range of values for which the percentage of the unique nucleic acid sequences specific for the sample indicates the expected number of unique nucleic acid sequences specific for the sample are found in the sample. Accordingly, a percentage that falls above or below an established error threshold can indicate an error in the method occurred and invalidate the sample. The error threshold can be between 0.01%-2.0%, between 0.05%-2.0%, or between 0.01%-1.0%. The error threshold can between 0.05%-1.0%.

Another particular advantage of the methods described herein is the assessment can be used to establish whether contamination occurred following an amplification step. For example, if a sample identifying nucleic acid sequence (e.g., a "barcode") is added to polynucleotides amplified during the methods described herein, assessing whether sample identifying nucleic acid sequences not assigned to a specific sample ("an unexpected sample identifying nucleic acid sequence") are present (e.g., assessing if incorrect barcodes associated with a sample/well are present) can be used as part of assessing whether the assay met a quality control standard. For example, the presence of an unexpected sample identifying nucleic acid sequence can indicate contamination and invalidate the sample.

A computer, as described herein, can be used to perform determination (e.g., sequencing) and assessment steps described herein.

The different methods of assessing quality control, such as determining if a method meets a contamination threshold, an error threshold, or a post-amplification threshold, are not mutually exclusive. For example, the method can include one of determining if a method meets a contamination threshold, an error threshold, or a post-amplification contamination threshold. In another example, the method can include all three of determining if a method meets a contamination threshold, an error threshold, and a post-amplification contamination threshold. In yet another example, the method can include determining if a method meets a contamination threshold and an error threshold, determining if a method meets a contamination threshold and a post-amplification contamination threshold, or determining if a method meets an error threshold and a post-amplification contamination threshold.

6.4. Examples

Below are examples of specific embodiments for carrying out the present invention. The examples are offered for illustrative purposes only, and are not intended to limit the scope of the present invention in any way. Efforts have been made to ensure accuracy with respect to numbers used (e.g., amounts, temperatures, etc.), but some experimental error and deviation should, of course, be allowed for.

The practice of the present invention will employ, unless otherwise indicated, conventional methods of protein chemistry, biochemistry, recombinant DNA techniques and pharmacology, within the skill of the art. Such techniques are explained fully in the literature. See, e.g., T. E. Creighton, *Proteins: Structures and Molecular Properties* (W. H. Freeman and Company, 1993); A. L. Lehninger, *Biochemistry* (Worth Publishers, Inc., current addition); Sambrook, et al., *Molecular Cloning: A Laboratory Manual* (2nd Edition, 1989); *Methods In Enzymology* (S. Colowick and N. Kaplan eds., Academic Press, Inc.); *Remington's Pharmaceutical Sciences,* 18th Edition (Easton, Pennsylvania: Mack Publishing Company, 1990); Carey and Sundberg *Advanced Organic Chemistry* $3^{rd}$ Ed. (Plenum Press) Vols A and B (1992).

6.4.1. Digital Serology Method 6.4.1.1. Overview

Digital Serology is a Next-generation Sequencing (NGS)-based assay similar to other biopanning assays in which peptide libraries are screened with human serum to map human antibody repertoires. The assay involves 4 main steps: 1) incubation of serum with the peptide library and affinity selection of library members expressing peptides that are specific to the antibody repertoire for each serum sample; 2) purification of plasmids that encode these peptides; 3) PCR amplification of the region of the plasmids encoding the peptides (amplicons) and barcoding of each sample with sample-specific primers (allowing samples to be pooled and sequenced together on a single NGS run); and 4) amplicon sequencing by NGS. Once the amplicons are sequenced, the data are demultiplexed and antibodies present in each serum sample are identified based on the peptide motifs to which they bind.

6.4.1.2. Methods

The methods described below are useful for the examples described herein but are not intended to be limiting. Methods useful for the present invention, e.g., digital serology including motif determination and motif analysis, are also described in more detail in Pantazes, et al. and international PCT application WO2017083874A1, each herein incorporated by reference for all they teach.

Serum Collection

Serum from healthy patients, as well as patients diagnosed with HIV or tuberculosis, were obtained from BioIVT, BBI Solutions, Proteogenex and Discovery Life Sciences.

Bacterial Surface Display Antibody Screen

A large, high-quality, bacterial-display, random, 12-mer peptide library composed of $8\times10^9$ independent transformants, was constructed using trinucleotide oligos to eliminate stop codons and normalize amino acid usage frequencies. The 12-mer peptide library was displayed on *E. coli* via the N-terminus of a previously reported, engineered protein scaffold (eCPX), as described in more detail in Rice, et al., herein incorporated by reference for all it teaches. Vectors, methods, and other tools useful in the *E. coli* surface displayed peptide library are described in more detail in issued U.S. Pat. No. 7,256,038, issued U.S. Pat. No. 8,293,685, issued U.S. Pat. No. 7,612,019, issued U.S. Pat. No. 8,361,933, issued U.S. Pat. No. 9,134,309, issued U.S. Pat. No. 9,062,107, issued U.S. Pat. No. 9,695,415, and U.S. published application US20160032279, each herein incorporated by reference for all they teach.

To remove *E. coli* binding antibodies from serum samples prior to library screening, an induced culture of cells expressing the library scaffold alone was incubated with diluted sera (*E. coli* strain MC1061 [FaraΔ 139 D (ara-leu) 7696 GalE15 GalK16 Δ (lac) X74 rpsL (StrR) hsdR2 (rK−mK+) mcrA mcrB1] was used with surface display vector pB33eCPX). eCPX cultures grown overnight at 37° C. with vigorous shaking (250 rpm) in LB (10 g tryptone, 5 g yeast extract, 10 g/L NaCl) supplemented with 34 µg/mL chloramphenicol (CM) and 0.2% glucose were collected by centrifugation, inoculated in fresh LB+CM, grown to an $OD_{600}=0.6$, and induced for 1 hour at 37° C. with 0.02% wt/vol L (+)-arabinose. After induction, cells were centrifuged at 3,000 relative centrifugal force (rcf) for 5 min., washed once with cold PBST (PBS+0.1% Tween 20), and resuspended in 750 µL PBST containing serum diluted 1:25 ($1\times10^{10}$ cells per depletion sample). Samples were incubated overnight at 4° C. with gentle mixing on an orbital shaker (20 rpm). Antibodies that bound to *E. coli* or the eCPX scaffold were removed by centrifugation of the incubated culture at 5,000 rcf for 5 min. twice, recovering the serum supernatant after each centrifugation. Depleted serum was stored at 4° C. for up to 2 weeks during use.

The bacterial display peptide library was used to screen and isolate peptide binders to antibodies in individual serum samples through Magnetic Activated Cell Sorting (MACS). The MACS screen employed magnetic selection to enrich the library for antibody binding peptides as well as reduce the library size suitable for the subsequent screening steps. A frozen aliquot of the library containing $10^{11}$ cells (>10× the expected diversity) was thawed and inoculated into 500 ml LB+CM. After growth to an $OD_{600}=0.6$ at 37° C. with 250 rpm shaking, the cells are induced with 0.02% wt/vol L (+)-arabinose for one hour using the same growth conditions. Cells ($5\times10^{10}$ per sample) were collected by centrifugation (3,000 rcf for 10 min.) and resuspended in 750 µL cold PBST. Prior to incubation with serum, cells were cleared of peptides that bind protein A/G by incubating cells with washed protein A/G magnetic beads (Pierce) at a ratio of one bead per 50 cells for 45 min. at 4° C. with gentle mixing. Magnetic separation for 5 min. (x2) was used to recover the unbound cells. Recovered cells from the supernatant are centrifuged, resuspended in diluted sera (1:25) and incubated for 45 min. at 4° C. with gentle mixing. Following serum incubation, cells were washed by centrifugation and resuspended in 750 µL cold PBST (x3). After the final resuspension, washed protein A/G magnetic beads were added at a ratio of one bead per 50 cells. After a 45 min. incubation with protein A/G beads at 4° C. with gentle mixing, a second magnetic separation isolated cells expressing peptides that bind to serum antibodies. The supernatant (unbound cells) was discarded and the separated cells/beads were washed with 750 µL cold PBST. 5 repeat washes were performed while the tube was being magnetized. After the last wash, the beads were resuspended in 1 mL of LB and inoculated into 25 mL LB+CM+glucose to suppress expression. The flask was grown overnight at 37° C. with shaking at 250) rpm.

Next Generation Sequencing

Cells grown overnight after the MACS enrichment were collected and plasmid was extracted using a plasmid miniprep kit (Qiagen). The random peptide region was amplified using a two-step PCR. For the first PCR step, the primers include adaptors specific to the Illumina sequencing platform with annealing regions that flank the random region (peptide library) of the eCPX scaffold. Bolded regions anneal to the eCPX scaffold, and nnnnn are 5 random degenerate bases that help the NGS protocol discriminate sequencing reads on the sequencing chip, particularly those sequences with a constant vector sequence ahead of the peptide encoding nucleotides.

Forward Primer (SEQ ID NO: 1):
TCGTCGGCAGCGTCAGATGTGTATAAGAGACAGnnnnnCCAGTCTGGCCA
GGG

Reverse Primer (SEQ ID NO: 2):
CCAGTACTACGGCATCACTGCTGTCTCTTATACACATCTCCGAGCCCACG
AGAC Products from the first PCR were purified after 25 rounds of PCR amplification (touchdown PCR) using Agencourt Ampure XP (Beckman Coulter) clean up beads. Resulting product was subjected to a second round of PCR using Illumina Nextera XT indexing primers (Illumina). These primers provide unique 8 base pair indicies on the 3 prime and 5 prime ends of the amplicons for tracking the sequences back to the sample used for screening and amplicon preparation. Amplicons were cleaned up as before after 8 rounds of PCR amplification (70° C. annealing temp). The final PCR product (amplicon) DNA concentration was measured using DNA high sensitivity reagent on a Qbit instrument (Life Technologies). All samples were normalized to 4 nM and pooled together into a sequencing library.

The pooled sample was diluted and loaded on to the NextSeq instrument. A 75 cycle high-output flow cell was used with single read (one direction) and dual indexing (both 5 prime and 3 prime indicies are sequenced). After sequencing was complete, the samples were automatically de-multiplexed using imputed sample identities with Illumina Nextera XT indicies.

Phenotype Determination and Disease Diagnosis

Following NGS analysis, samples were analyzed for enrichment for each motif in a panel of peptide motifs that were previously identified as diagnostic motifs for specific diseases. The enrichment was calculated by dividing the number of observed instances for each motif by the number of expected instances. A z-score for each motif was calculated where each z-score indicates the enrichment value minus the mean enrichment for all samples divided by the standard deviation of all samples. To calculate a diagnostic score, the z-scores for each motif were summed for specific disease. Diagnostic thresholds, e.g., whether a sample was considered to be positive for a disease, were established for each condition balancing sensitivity and specificity.

6.4.2. Assay for Quality Control Using Flag Epitope
6.4.2.1. Overview

The general method of an example of quality control assessment using Quality Control ("QC") index clones follows the steps of 1) spiking a protein display library with a QC index clone(s) that expresses a control epitope tag fused to an amino acid sequence unique to each specific QC index clone 2) spiking an antibody containing sample with a control antibody that recognizes the control epitope tag 3) incubating the spiked protein display library with the spiked sample, during which the antibody specific for the control epitope tag will bind to QC index clone(s) 4) capturing all antibodies bound to, during which QC index clone(s) bound by the control antibodies are captured along with peptide clones that bind to antibodies present in the sample 5) purifying, amplifying, and sequencing the plasmids in the captured library, including the plasmid expressing control epitope tag as well as those plasmids expressing peptides bound by other antibodies in the sample 6) analyzing the number of sequencing reads associated with the QC index clones, in particular the number of clones expressing the unique amino acid sequence specific to each clone, to assess whether the sample preparation and analysis meets an established threshold quality. The concentration of the control antibody and the number of QC index clones spiked into the library are chosen such that a failure at any step of the assay will be detected by a change in the number of QC clones captured and can be adjusted for individual screens, for example depending upon the size of the library used for screening.

6.4.2.2. Methods
QC Index Construction

QC index clones were constructed in the context of the bacterial display library scaffold. For each QC index clone (i.e., control vector), a QC index peptide was constructed comprised of an amino acid sequence encoding the Flag epitope tag DYKDDDDK (SEQ ID NO:3) common to all QC index clones (i.e., the control binding target) and was followed by a four amino acid unique peptide tag that is specific to each clone (i.e., the unique peptide sequence encoded by a unique nucleic acid sequence). The unique peptides tag for each QC index clone was comprised of the four amino acids TSNQ (SEQ ID NO:83) rearranged to form an amino acid sequence unique to each clone. The same four amino acids were used for each unique amino acid sequence to reduce introducing expression differences or other properties (e.g., hydrophobicity) that potentially could result from using different amino acids. Clones were also designed such that the DNA sequences (i.e., the unique nucleic acid sequences) differ by a minimum of four bases to reduce the likelihood that sequencing errors could result in conversion of one QC index to a different index.

Library Screening with QC Index Clones

A unique pair of QC index clones (i.e., the one or more control vectors) were spiked into a given well (or tube) containing the peptide display library sample (i.e., the library of nucleic acid sequences encoding a library of peptides) to be incubated with a given serum sample. For each QC index clone, $1\times10^6$ copies were added and at a final ratio of $1.3\times10^{-5}$ QC clones per total library clones. Flag antibody (i.e., the control binding molecule) [Absolute Antibody anti-Flag DDDDK (SEQ ID NO:84) M2.1, Cat. #AB00739-10.0] was spiked into the serum samples (normal control serum) at a final concentration of 2 nM. The Flag antibody spiked serum was then incubated with the QC index spiked bacterial library. Antibodies, including both Flag antibodies and other serum antibodies, and their bound peptide clones were subsequently captured by protein A/G magnetic beads (i.e., the capture entity) and magnetically separated (i.e., isolated) from the unbound library members using the MACS methods previously described herein. Plasmid purification, amplification, and sequencing by NGS was performed using the methods previously described herein (i.e. the determining step). Total de-multiplexed sequencing reads for each unique peptides tag specific to each QC index clone was quantitated.

6.4.2.3. QC Index Clone Design Using 4 Amino Acid Unique Peptide Tag

QC index clones were constructed as described above. The amino acid and DNA sequence for each of the possible 24 possible Flag-QC index peptides using various rearrangements of the amino acids TSNQ (SEQ ID NO:83) for the unique peptide tag are shown in Table 1. The nucleotide sequence for each Flag-QC index peptide in the context of the bacterial surface display expression vector is shown in Table 2. A unique pair of the 24 QC indices was added to each specific well. For example, FIG. 5 illustrates a 96-well plate formatted with 10 unique QC clones (QC1-8, QC11, and QC12) arrayed by 8 unique clones (QC13-15 and QC19-23) to generate 80 unique QC pairs. The general QC index system using the Flag epitope/antibody system and 2 QC index clones per sample/well is outlined in FIG. 1.

TABLE 1

Possible QC Index Clones Using TSNQ (SEQ ID NO: 83) for Unique Peptide Tag

| Clone | Amino acid Sequence | SEQ ID NO | DNA Sequence | SEQ ID NO |
|---|---|---|---|---|
| QC1 | DYKDDDDKTSNQ | 10 | GACTATAAGGACGATGATGACAAAACAAGTAATCAG | 34 |
| QC2 | DYKDDDDKTSQN | 11 | GATTACAAGGATGATGACGATAAAACATCGCAAAAT | 35 |
| QC3 | DYKDDDDKTQNS | 12 | GATTACAAAGACGATGACGACAAAACCCAGAACTCG | 36 |
| QC4 | DYKDDDDKTQSN | 13 | GACTATAAAGATGACGATGACAAGACGCAAAGCAAT | 37 |
| QC5 | DYKDDDDKTNQS | 14 | GACTATAAAGACGACGATGATAAAACTAATCAATCA | 38 |
| QC6 | DYKDDDDKTNSQ | 15 | GACTATAAAGATGACGATGATAAGACTAACTCGCAA | 39 |
| QC7 | DYKDDDDKNSTQ | 16 | GATTACAAGGATGATGATGACAAAAATAGCACGCAA | 40 |
| QC8 | DYKDDDDKNSQT | 17 | GACTATAAGGATGACGACGACAAAAACTCCCAAACA | 41 |
| QC9 | DYKDDDDKNTQS | 18 | GATTACAAGGACGACGACGATAAAAACACACAAAGT | 42 |
| QC10 | DYKDDDDKNTSQ | 19 | GACTATAAAGACGACGATGATAAGAATACCTCTCAA | 43 |
| QC11 | DYKDDDDKNQTS | 20 | GACTACAAAGACGATGACGACAAAAATCAGACGAGT | 44 |
| QC12 | DYKDDDDKNQST | 21 | GACTATAAAGATGACGACGATAAGAATCAGTCAACT | 45 |
| QC13 | DYKDDDDKQTNS | 22 | GACTATAAGGATGATGACGATAAACAGACGAACAGT | 46 |
| QC14 | DYKDDDDKQTSN | 23 | GATTACAAAGATGACGATGACAAACAAACAAGCAAT | 47 |
| QC15 | DYKDDDDKQSNT | 24 | GATTACAAGGACGACGATGATAAGCAGTCCAATACC | 48 |
| QC16 | DYKDDDDKQSTN | 25 | GACTATAAGGATGATGATGACAAACAATCCACGAAT | 49 |

TABLE 1-continued

Possible QC Index Clones Using TSNQ (SEQ ID NO: 83) for Unique Peptide Tag

| Clone | Amino acid Sequence | SEQ ID NO | DNA Sequence | SEQ ID NO |
|---|---|---|---|---|
| QC17 | DYKDDDDKQNTS | 26 | GACTATAAAGATGACGATGATAAGCAAAACACCTCC | 50 |
| QC18 | DYKDDDDKQNST | 27 | GACTACAAAGACGACGACGATAAACAGAACAGCACA | 51 |
| QC19 | DYKDDDDKSQNT | 28 | GACTATAAAGATGATGATGACAAATCACAGAATACA | 52 |
| QC20 | DYKDDDDKSQTN | 29 | GATTACAAGGATGACGATGACAAGTCACAGACTAAT | 53 |
| QC21 | DYKDDDDKSNTQ | 30 | GACTACAAAGACGACGACGATAAGTCCAATACTCAA | 54 |
| QC22 | DYKDDDDKSNQT | 31 | GATTACAAGGATGATGATGACAAAAGCAATCAAACG | 55 |
| QC23 | DYKDDDDKSTQN | 32 | GACTATAAGGACGACGACGACAAATCAACTCAAAAC | 56 |
| QC24 | DYKDDDDKSTNQ | 33 | GACTACAAGGATGACGATGATAAGTCAACTAATCAA | 57 |

TABLE 2

Possible QC Index Clones Using TSNQ (SEQ ID NO: 83) in Expression Vector Context

| Clone | DNA Sequence | SEQ ID NO |
|---|---|---|
| QC1 | ACTTCCGTAGCTGGCCAGTCTGGCCAGGGTGGAGACTATAAGGACGATGATGACAAAACAAGTAATCAGGGAGGGCAGTCTGGGCAGTCTG | 58 |
| QC2 | ACTTCCGTAGCTGGCCAGTCTGGCCAGGGTGGAGATTACAAGGATGATGACGATAAAACATCGCAAAATGGAGGGCAGTCTGGGCAGTCTG | 59 |
| QC3 | ACTTCCGTAGCTGGCCAGTCTGGCCAGGGTGGAGATTACAAAGACGATGACGACAAAACCCAGAACTCGGGAGGGCAGTCTGGGCAGTCTG | 60 |
| QC4 | ACTTCCGTAGCTGGCCAGTCTGGCCAGGGTGGAGACTATAAAGATGACGATGACAAGACGCAAAGCAATGGAGGGCAGTCTGGGCAGTCTG | 61 |
| QC5 | ACTTCCGTAGCTGGCCAGTCTGGCCAGGGTGGAGACTATAAAGACGACGATGATAAAACTAATCAATCAGGAGGGCAGTCTGGGCAGTCTG | 62 |
| QC6 | ACTTCCGTAGCTGGCCAGTCTGGCCAGGGTGGAGACTATAAAGATGACGATGATAAGACTAACTCGCAAGGAGGGCAGTCTGGGCAGTCTG | 63 |
| QC7 | ACTTCCGTAGCTGGCCAGTCTGGCCAGGGTGGAGATTACAAGGATGATGATGACAAAAATAGCACGCAAGGAGGGCAGTCTGGGCAGTCTG | 64 |
| QC8 | ACTTCCGTAGCTGGCCAGTCTGGCCAGGGTGGAGACTATAAGGATGACGACGACAAAAACTCCCAAACAGGAGGGCAGTCTGGGCAGTCTG | 65 |
| QC9 | ACTTCCGTAGCTGGCCAGTCTGGCCAGGGTGGAGATTACAAGGACGACGACGATAAAAACACACAAAGTGGAGGGCAGTCTGGGCAGTCTG | 66 |
| QC10 | ACTTCCGTAGCTGGCCAGTCTGGCCAGGGTGGAGACTATAAAGACGACGATGATAAGAATACCTCTCAAGGAGGGCAGTCTGGGCAGTCTG | 67 |
| QC11 | ACTTCCGTAGCTGGCCAGTCTGGCCAGGGTGGAGACTACAAAGACGATGACGACAAAAATCAGACGAGTGGAGGGCAGTCTGGGCAGTCTG | 68 |
| QC12 | ACTTCCGTAGCTGGCCAGTCTGGCCAGGGTGGAGACTATAAAGATGACGACGATAAGAATCAGTCAACTGGAGGGCAGTCTGGGCAGTCTG | 69 |
| QC13 | ACTTCCGTAGCTGGCCAGTCTGGCCAGGGTGGAGACTATAAGGATGATGACGATAAACAGACGAACAGTGGAGGGCAGTCTGGGCAGTCTG | 70 |
| QC14 | ACTTCCGTAGCTGGCCAGTCTGGCCAGGGTGGAGATTACAAAGATGACGATGACAAACAAACAAGCAATGGAGGGCAGTCTGGGCAGTCTG | 71 |
| QC15 | ACTTCCGTAGCTGGCCAGTCTGGCCAGGGTGGAGATTACAAGGACGACGATGATAAGCAGTCCAATACCGGAGGGCAGTCTGGGCAGTCTG | 72 |
| QC16 | ACTTCCGTAGCTGGCCAGTCTGGCCAGGGTGGAGACTATAAGGATGATGATGACAAACAATCCACGAATGGAGGGCAGTCTGGGCAGTCTG | 73 |

TABLE 2-continued

Possible QC Index Clones Using TSNQ (SEQ ID NO: 83) in Expression Vector Context

| Clone | DNA Sequence | SEQ ID NO |
|---|---|---|
| QC17 | ACTTCCGTAGCTGGCCAGTCTGGCCAGGGTGGAGACTATAAAGATGACGATGATAAGCAAAACACCTCCGGAGGGCAGTCTGGGCAGTCTG | 74 |
| QC18 | ACTTCCGTAGCTGGCCAGTCTGGCCAGGGTGGAGACTACAAAGACGACGACGATAAACAGAACAGCACAGGAGGGCAGTCTGGGCAGTCTG | 75 |
| QC19 | ACTTCCGTAGCTGGCCAGTCTGGCCAGGGTGGAGACTATAAAGATGATGATGACAAATCACAGAATACAGGAGGGCAGTCTGGGCAGTCTG | 76 |
| QC20 | ACTTCCGTAGCTGGCCAGTCTGGCCAGGGTGGAGATTACAAGGATGACGATGACAAGTCACAGACTAATGGAGGGCAGTCTGGGCAGTCTG | 77 |
| QC21 | ACTTCCGTAGCTGGCCAGTCTGGCCAGGGTGGAGACTACAAAGACGACGACGATAAGTCCAATACTCAAGGAGGGCAGTCTGGGCAGTCTG | 78 |
| QC22 | ACTTCCGTAGCTGGCCAGTCTGGCCAGGGTGGAGATTACAAGGATGATGATGACAAAAGCAATCAAACGGGAGGGCAGTCTGGGCAGTCTG | 79 |
| QC23 | ACTTCCGTAGCTGGCCAGTCTGGCCAGGGTGGAGACTATAAGGACGACGACGACAAATCAACTCAAAACGGAGGGCAGTCTGGGCAGTCTG | 80 |
| QC24 | ACTTCCGTAGCTGGCCAGTCTGGCCAGGGTGGAGACTACAAGGATGACGATGATAAGTCAACTAATCAAGGAGGGCAGTCTGGGCAGTCTG | 81 |

6.4.2.4. Determination of Upper and Lower Threshold QC Index Counts for Quality Control A series of Digital Serology experiments was performed using QC index clones to establish threshold criteria for assessing whether a sample was properly processed, e.g., efficient pull down of antibodies, purification of expression vectors, and amplification of DNA, avoidance of contamination etc.

To establish QC index assessment criteria (i.e., a quality control standard), the Digital Serology assay was performed under standard conditions or under conditions to mimic assay failure that might occur during screening. These included poor or no induction of bacterial surface peptides, no serum added to the well or addition of the wrong type of magnetic beads during the capture step.

Samples in a 96-well plate format were processed and the QC index counts were tabulated for each condition. For each well, a pair of QC index clones were used in the experiments, as described above. The results are shown in FIG. 2. QC counts are expressed as the percentage of QC counts per total number of NGS reads. The percentage for each QC index in the pair is shown. The majority of samples processed under normal conditions ("Normal Plate 12" and "Normal Plate 13") clustered between a QC clone/total NGS read percentage of 0.05% and 1.0%. Sample wells in which serum was omitted ("No Serum") or in which libraries were uninduced (i.e., no surface displayed peptide was expressed, "Uninduced") exhibited higher QC index/total read percentages of ≥1%. High QC index/total read percentages indicated insufficient capture of serum antibodies in the assay, resulting in more Flag antibody-QC index pairs binding to the beads. In samples in which streptavidin beads ("SA Beads") were used that do not efficiently capture antibodies, QC clone/total read percentages were <0.01%. The percentage reflects the original ratio of QC clones spiked in the sample indicating insufficient capture of both serum antibodies and the Flag QC antibody. Serum from Lyme disease positive individuals were used in these experiments, and all samples between 0.05-1.0% QC index/total reads were accurately diagnosed based on summed z-scores when motifs analysis was performed using a previously established Lyme disease panel (data not shown). Thus, comparing properly processed samples to simulated failed sample preparation conditions (no serum antibodies, no library peptide expression, inefficient antibody capture, etc.) established an error threshold range with lower and upper values of 0.05% and 1.0%, respectively, as cut-offs to assess whether data from a sample/well was considered valid (i.e., met a quality control standard). In other words, QC clone/total read percentages ("a percentage of the unique nucleic acid sequences specific for a sample relative to a total number of nucleic acid sequences") falling outside the error threshold range of 0.05% and 1.0% were considered to have failed meeting the quality control standard.

6.4.2.5. Identification of Well Contamination Using QC Index Clones

QC index pairs are unique identifiers for each sample well and, as such, the presence of the wrong index pair can indicate whether contamination has occurred at any point during the assay. For example, during the wash steps of the protocol described above, it is possible that a sample from one well can splash into an adjacent well resulting in cross-contamination.

To establish that contamination can be detected by the presence of the wrong QC index clone, wells containing control sera were contaminated during wash steps in the assay in either the 1$^{st}$ wash or the bead wash with 10%, 5%, 2% or 1% of a disease well sample, with 5 control wells contaminated for each condition. After incubation of serum with the library, for the first wash the cells were centrifuged, the unbound serum supernatant were removed, and each well resuspended with 750 μL of PBST. After this initial resuspension, an appropriate amount of a sample containing the contaminating QC indices was added for the "contamination at 1$^{st}$ wash" samples. The wash process was repeated three times. After the final washing step, cells were resuspended and incubated with beads. The cell/bead mixture was washed with 750 μL PBST and the beads collected. After resuspension at this step, an appropriate amount of a sample containing the contaminating QC indices was added for "contamination at beads wash" samples. An additional four washes of the beads with 750 µL PBST was performed. Disease sera from patients with HIV and Tuberculosis were used to contaminate control sera. Samples were processed using standard Digital Serology methods.

The percent of contaminating QC index clones ("unique nucleic acid sequences not specific for the sample") determined by NGS present in each sample relative to the correct index were calculated (FIG. 3). Presence of low numbers of QC indices considered contaminating were present in background wells, likely as a result of PCR errors, and were generally below 10 counts for any given index. In contrast, contamination with as little as 1% of a disease sample contaminating QC index clones at both wash steps in the assay was detectable above background. Increased contamination also resulted in an increased percentage of contaminating QC index clones. Thus, spiking QC index clones into each peptide display library at an amount of $1 \times 10^6$ for each QC index clone and at a final ratio of $1.3 \times 10^{-5}$ QC clones per total library clones was sufficient to detect contamination above background of as low as 1%. Accordingly, the example described here established a contamination threshold of 1%, where a percent of contaminating QC index clones above the contamination threshold indicated contamination and potentially would fail to meet a quality control standard.

To determine the impact of contamination on diagnostic accuracy, contamination of healthy sera with various levels of contaminating disease sera was evaluated for the potential to produce a false positive diagnosis above the established diagnostic cut-off. As shown in FIG. 4, control healthy sera was contaminated at the different assay stages as described above with sera from known to be positive for tuberculosis (TB+, FIG. 4a) or HIV (HIV+, FIG. 4B). Each disease sera also contained QC index clones specific to each sera. Diagnostic scores for the specific disease that was the source of the contamination (measured as the sum of z-scores of previously established disease specific motifs) were calculated for the motifs bound by antibodies in the contaminated healthy serum. In addition, the number of QC index counts specific for healthy sera as well as those specific for each of the disease sera were calculated. The percent of contaminating QC index clones was calculated and is shown in FIG. 4 above each sample. In healthy sera samples with 5 and 10% contamination, the diagnostic scores were elevated relative to controls with no contamination. In particular, a 10% contamination of with HIV positive sera resulted in a false positive diagnostic score. In contrast, samples with 1% or 2% contamination were all diagnostically negative with similar diagnostic scores to those without contamination ("No contamination"). In samples contaminated at the first wash stage with either 1% TB positive or HIV positive sera, the calculated number of QC index clones was ~2%. Together, the data demonstrate a 1% contamination at different stages of sample preparation resulted in a detectable QC index contamination level that remained less than 2% while not affecting diagnostic accuracy. Thus, samples below 2% observed QC index contamination were considered diagnostically valid. Accordingly, the example described here established another contamination threshold of 2%, where a percent of contaminating QC index clones below the contamination threshold indicated the sample analysis would be considered diagnostically valid and meet a quality control standard. In contrast, a percent of contaminating QC index clones above the contamination threshold could influence diagnostically validity and fail to meet a quality control standard.

7. EQUIVALENTS

While the invention has been particularly shown and described with reference to a preferred embodiment and various alternate embodiments, it will be understood by persons skilled in the relevant art that various changes in form and details can be made therein without departing from the spirit and scope of the invention.

8. INCORPORATION BY REFERENCE

All references, issued patents and patent applications cited within the body of the instant specification are hereby incorporated by reference in their entirety, for all purposes.

9. REFERENCES CITED

Endrullat C, Glökler J, Franke P, Frohme M. (2016) Standardization and quality management in next-generation sequencing. Appl Transl Genom. 10:2-9.

Rice, J. J. & Daugherty, P. S. Directed evolution of a biterminal bacterial display scaffold enhances the display of diverse peptides. Protein Eng. Des. Sel. 21, 435-442 (2008).

Pantazes, R. J. et al. Identification of disease-specific motifs in the antibody specificity repertoire via next-generation sequencing. Sci. Rep. 6, 30312; doi: 10.1038/srep30312 (2016).

Dayhoff, M. & Schwartz, R. A Model of Evolutionary Change in Proteins. Atlas protein Seq. Struct. 345-352 doi: 10.1.1.145.4315 (1978).

What is claimed is:

1. A peptide expression library composition comprising:
   a) a library of nucleic acid sequences encoding a library of peptides;
   b) one or more control vectors comprising:
      1) A nucleic acid sequence encoding a control binding target of a control binding molecule, wherein the control binding target is identical for each of the control vectors, and
      2) A unique nucleic acid sequence, wherein the unique nucleic acid sequence is specific for each of the control vectors.

2. A peptide library composition comprising:
   a) a library of nucleic acid sequences encoding a library of random peptides;
   b) two control vectors, each comprising:
      1) A nucleic acid sequence encoding an epitope sequence that is a known binding target of a control binding molecule, wherein the control binding molecule comprises an antibody or fragment thereof, wherein the epitope sequence is identical for each of the control vectors, and
      2) A unique nucleic acid sequence, wherein the unique nucleic acid sequence is specific for each of the control vectors, wherein the unique nucleic acid sequence encodes a unique peptide sequence capable of being expressed as part of a polypeptide comprising the epitope sequence, wherein each of the unique peptide sequences comprises an identical amino acid composition, and wherein each of the unique nucleic acid sequences differ by at least 2 nucleotides, and
   c) two or more array surfaces,
   wherein the library of random peptides and the epitope sequence are capable of being expressed, and wherein each of the array surfaces is configured to display multiple copies of:
      1) One of the random peptides, or
      2) The epitope sequence encoded by one of the control vectors.

3. The composition of claim 1, the composition further comprising:
   two or more array surfaces, wherein each of the array surfaces is configured to display one or more copies of either:
      1) One of the peptides of the library of peptides, or
      2) the control binding target encoded by one of the control vectors.

4. The composition of claim 1, wherein the library of peptides is a random peptide library.

5. The composition of claim 1, wherein the library of peptides is selected from the group consisting of: a bacterial expression library, a yeast expression library, a bacteriophage expression library, and a mammalian expression library.

6. The composition of claim 1, wherein the control binding target comprises a defined peptide sequence.

7. The composition of claim 6, wherein the defined peptide sequence comprises an epitope sequence.

8. The composition of claim 7, wherein the epitope sequence is not derived from an antigen generally encountered in a human population.

9. The composition of claim 7, wherein the epitope sequence is selected from the group consisting of: FLAG (DYKDDDDK, SEQ ID NO:3), Myc (EQKLISEEDL, SEQ ID NO:4), HA (YPYDVPDYA, SEQ ID NO:5), His (HHHHHH, SEQ ID NO:6), 3X-FLAG (DYKDHDGDYKDHDIDYKDDDK, SEQ ID NO:7), V5 (GKPIPNPLLGLDST, SEQ ID NO:8), and VSV-G (YTDIEMNRLGK, SEQ ID NO:9).

10. The composition of claim 1, wherein the control binding molecule comprises an antibody or fragment thereof.

11. The composition of claim 1, wherein each of the unique nucleic acid sequences is at least 4, 5, 6, 7, 8, 9, 10, 11, 12, 13, 14, 15, 16, 17, 18, 19, 20, 21, 22, 23, 24, 25, 26, 27, 28, 29, or 30 nucleotides in length.

12. The composition of claim 1, wherein each of the unique nucleic acid sequences is an identical defined length.

13. The composition of claim 1, wherein each of the unique nucleic acid sequences differ by at least 2, at least 3, at least 4, at least 5, at least 6, at least 7, at least 8, at least 9, at least 10-15, at least 15-20, or at least 20-30 nucleotides.

14. The composition of claim 1, wherein the unique nucleic acid sequence encodes a unique peptide sequence.

15. The composition of claim 14, wherein the control binding target comprises a defined peptide sequence, and the unique peptide sequence is capable of being expressed as part of a polypeptide comprising the defined peptide sequence.

16. The composition of claim 14, wherein each of the unique peptide sequences is an identical defined length.

17. The composition of claim 14, wherein at least 2 of the unique peptide sequences comprises an identical amino acid composition.

18. The composition of claim 17, wherein each of the unique peptide sequences comprises an identical amino acid composition.

19. The composition of claim 17, wherein an order of amino acids in the identical amino acid composition is unique for each of the unique peptide sequences comprising the identical amino acid composition.

20. The composition of claim 17, wherein the number of unique amino acids in the unique peptide sequences with the identical amino acid composition is equivalent to a defined length of the unique peptide sequence.

21. The composition of claim 1, wherein a total number of nucleic acid sequences in the library of nucleic acid sequences and a total number of each of the one or more control vectors is at a defined ratio.

22. The composition of claim 1, wherein the composition further comprises one or more second control vectors, each of the second control vectors comprising:
   1) A nucleic acid sequence encoding a second control binding target of a second control binding molecule, wherein the second control binding target is identical for each of the second control vectors, and
   2) A unique nucleic acid sequence, wherein the unique nucleic acid sequence is specific for each of the second control vectors.

23. The composition of claim 3, wherein the two or more array surfaces comprises a biological entity surface.

24. The composition of claim 1, wherein the nucleic acid sequences encoding the library of peptides, the nucleic acid sequences encoding the control binding targets, and the unique nucleic acid sequences each further comprise polymerase chain reaction (PCR) primer target sequences configured for amplification of the nucleic acid sequences encoding the library of peptides, the nucleic acid sequences encoding the control binding targets, and the unique nucleic acid sequences.

25. A composition comprising two or more, 2, 3, 4, 5, 6, 7, 8, 9, 10-15, 16-24, 24-48, 48-96, or 96-384 of the peptide expression library compositions of claim 1, wherein each of the peptide expression library compositions is in a separate container.

26. The composition of claim 25, wherein the unique nucleic acid sequence is unique for each of the two or more of the peptide expression library compositions.

27. The composition of claim 25, wherein each of the two or more of the peptide expression library compositions comprise two or more control vectors, wherein a combination of the unique nucleic acid sequences associated with the two or more control vectors are configured to uniquely identify each of the two or more of the peptide expression library compositions.

28. A kit comprising the peptide expression library composition of claim 1 and instructions for use.

29. A method of manufacturing the peptide expression library composition of claim 1.

30. A method of assay quality control comprising the steps of:
   a) providing a sample known or suspected to have specimen binding molecules,
   b) providing a peptide expression library composition comprising:
      A) a library of nucleic acid sequences encoding a library of peptides;
      B) one or more control vectors comprising:
         1) A nucleic acid sequence encoding a control binding target of a control binding molecule, wherein the control binding target is identical for each of the control vectors, and
         2) A unique nucleic acid sequence, wherein the unique nucleic acid sequence is specific for each of the control vectors; and
      C) two or more array surfaces, wherein each of the array surfaces is configured to display one or more copies of either:
         1) One of the peptides of the library of peptides, or
         2) The control binding target encoded by one of the control vectors,
      wherein the library of peptides is expressed, the control binding target is expressed, and wherein each of the array surfaces displays one or more copies of:
         1) One of the peptides of the library of peptides, or
         2) The control binding target, and
      wherein the unique nucleic acid sequences of the one or more control vectors is specific for the sample;
   c) providing the control binding molecule, and
   d) contacting the sample with the peptide expression library composition and the control binding molecule under conditions that promote binding of the control binding molecule to the control binding target.

* * * * *